(12) United States Patent
Wickline et al.

(10) Patent No.: US 10,758,627 B2
(45) Date of Patent: Sep. 1, 2020

(54) PEPTIDE-POLYNUCLEOTIDE COMPLEX FOR POLYNUCLEOTIDE TRANSFECTION

(71) Applicant: Washington University, St. Louis, MO (US)

(72) Inventors: Samuel A. Wickline, St. Louis, MO (US); Kirk Hou, St. Louis, MO (US)

(73) Assignee: Washington University, St. Louis, MO (US)

( * ) Notice: Subject to any disclaimer, the term of this patent is extended or adjusted under 35 U.S.C. 154(b) by 382 days.

(21) Appl. No.: 15/738,478

(22) PCT Filed: Jul. 1, 2016

(86) PCT No.: PCT/US2016/040678
§ 371 (c)(1),
(2) Date: Dec. 20, 2017

(87) PCT Pub. No.: WO2017/004512
PCT Pub. Date: Jan. 5, 2017

(65) Prior Publication Data
US 2020/0046844 A1    Feb. 13, 2020

Related U.S. Application Data

(60) Provisional application No. 62/187,979, filed on Jul. 2, 2015.

(51) Int. Cl.
| | | |
|---|---|---|
| *A61K 47/64* | (2017.01) | |
| *A61K 31/7105* | (2006.01) | |
| *A61K 31/713* | (2006.01) | |
| *C07K 7/08* | (2006.01) | |
| *C07K 19/00* | (2006.01) | |
| *A61K 38/00* | (2006.01) | |
| *C12N 15/11* | (2006.01) | |

(52) U.S. Cl.
CPC ........ *A61K 47/6455* (2017.08); *A61K 31/713* (2013.01); *A61K 31/7105* (2013.01); *C07K 7/08* (2013.01); *C07K 19/00* (2013.01); *C12N 15/111* (2013.01); *A61K 38/00* (2013.01); *C12N 2310/14* (2013.01); *C12N 2320/32* (2013.01)

(58) Field of Classification Search
None
See application file for complete search history.

(56) References Cited

U.S. PATENT DOCUMENTS

| | | |
|---|---|---|
| 7,098,032 B2 | 8/2006 | Trubetskoy et al. |
| 7,446,099 B2 | 11/2008 | Van et al. |
| 7,795,380 B2 | 9/2010 | Rice et al. |
| 8,501,930 B2 | 8/2013 | Rozema et al. |
| 8,617,516 B2 | 12/2013 | Wickline et al. |
| 9,987,371 B2 | 6/2018 | Wickline et al. |
| 2005/0191746 A1 | 9/2005 | Van et al. |
| 2007/0275923 A1 | 11/2007 | Chen et al. |
| 2011/0123438 A1 | 5/2011 | Wickline et al. |
| 2015/0314013 A1 | 11/2015 | Wickline et al. |

FOREIGN PATENT DOCUMENTS

| | | |
|---|---|---|
| WO | 2005085458 A2 | 9/2005 |
| WO | 2007069090 A2 | 6/2007 |
| WO | 2011020188 A1 | 2/2011 |
| WO | 2014107596 A1 | 7/2014 |
| WO | 2017004512 A1 | 1/2017 |

OTHER PUBLICATIONS

Chen, B. et al., "Characterization and evaluation of a peptide-based siRNA delivery system in vitro," Drug Deliv. Transl. Res., 2017, pp. 507-515, vol. 7, Springer.
Extended European Search Report dated Dec. 7, 2016 from related European Patent Application No. 14735277.7; 21 pgs.
Hou, K. et al., "A novel mellitin-derived peptide nanoparticle delivery system for STAT3 siRNA mediated killing of B16 melanoma cells," The FASEB Journal, Apr. 2012, vol. 26, No. 1, Supplement 1037.4.
Hou, K. et al., "A role for peptides in overcoming endosomal entrapment in siRNA delivery—a focus on melittin," Biotechnology Advances, 2015, pp. 931-940, vol. 33.
Hou, K. et al., "Mechanisms of Nanoparticle Mediated siRNA Transfection by Melittin-Derived Peptides," NIH Public Access Author Manuscript, pp. 1-21, ACS Nano., Oct. 22, 2013, pp. 8605-8615, vol. 7, No. 10.
Hou, K. et al., "Melittin Derived Peptides for Nanoparticle Based siRNA Transfection," NIH Public Access Author Manuscript, pp. 1-20, Biomaterials, Apr. 2013, pp. 3110-3119, vol. 34, No. 12.
International Search Report and Written Opinion dated May 7, 2014 from related International Patent Application No. PCT/US2014/010212; 8 pgs.
International Search Report and Written Opinion dated Oct. 4, 2016 from related International Patent Application No. PCT/US2016/040678; 10 pgs.
Lee, U. et al., "Dual knockdown of p65 and p50 subunits of NF-kappaB by siRNA inhibits the induction of inflammatory cytokines and significantly enhance apoptosis in human primary synoviocytes treated with tumor necrosis factor-alpha," Mol. Biol. Rep., 2008, pp. 291-298, vol. 35, No. 3, Springer Science+Business Media B.V.
Lochmann, D. et al., "Albumin-protamine-oligonucleotide nanoparticles as a new antisense delivery system. Part 1: Physicochemical characterization," European Journal of Pharmaceutics and Biopharmaceutics, 2005, pp. 419-429, vol. 59, No. 3.
Noguchi, H. et al., "Protein Transduction Technology: A Novel Therapeutic Perspective," Acta Med. Okayama, 2006, pp. 1-11, vol. 60, No. 1, Okayama University Medical School, Japan.

(Continued)

*Primary Examiner* — Richard A Schnizer
(74) *Attorney, Agent, or Firm* — Polsinelli PC

(57) ABSTRACT

A pharmaceutical composition comprising a peptide-polynucleotide complex, and methods of use thereof.

20 Claims, No Drawings
Specification includes a Sequence Listing.

(56) References Cited

OTHER PUBLICATIONS

Notice of Allowance dated Dec. 22, 2016 from related U.S. Appl. No. 14/790,408; 5 pgs.
Notice of Allowance dated Feb. 6, 2018 from related U.S. Appl. No. 14/790,408; 5 pgs.
Office Action dated Jul. 19, 2017 from related Australian Patent Application No. 2014204012; 5 pgs.
Office Action dated Aug. 23, 2016 from related Canadian Patent Application No. 2,896,834; 5 pgs.
Office Action dated May 26, 2016 from related U.S. Appl. No. 14/790,408; 5 pgs.
Office Action dated Nov. 23, 2016 from related U.S. Appl. No. 14/790,408; 5 pgs.
Office Action dated Aug. 28, 2017 from related U.S. Appl. No. 14/790,408; 6 pgs.
Office Action dated Sep. 5, 2017 from related Japanese Patent Application No. 2015-551782, 5 pgs., with English translation.
Office Action dated Sep. 25, 2017 from related Canadian Patent Application No. 2,896,834; 3 pgs.
Ohtsuki, T. et al., "Intracellular introduction of RNA by carrier peptide," J. Japanese Biochem. Soc., 2009, pp. 110-112, vol. 81, No. 2, with English translation.
Partial Supplementary European Search Report dated Aug. 9, 2016 from related European Patent Application No. 14735277.7; 10 pgs.
Salomone, F. et al., "In Vitro Efficient Transfection by CM18-Tat11 Hybrid Peptide: A New Tool for Gene-Delivery Applications," PLoS One, Jul. 29, 2013, pp. 1-11, vol. 8, No. 7, e70108.
Takabe, W. et al., "Oscillatory Shear Stress Induces Mitochondrial Superoxide Production: Implication of NADPH Oxidase and c-Jun NH2-Terminal Kinase Signaling,"Antioxidants & Redox Signaling, Jan. 1, 2011, pp. 1379-1388, vol. 15, No. 5.
Tian, F. et al., "A small interfering RNA targeting NF-B p65 alone or combined with 5-FU inhibits growth of esophageal squamous cell carcinoma in nude mice," Pathology—Research and Practice, Oct. 30, 2012, pp. 32-38, vol. 208, No. 1.
Wu, Z-W. et al., "Recent progress in copolymer-mediated siRNA delivery," J. Drug Targeting, 2012, pp. 551-560, vol. 20, No. 7, Taylor & Francis.
Xu, Y. et al., "Targeting Stat3 suppresses growth of U251 cell-derived tumours in nude mice," J. Clinical Neuroscience, Mar. 1, 2012, pp. 443-446, vol. 19, No. 3.
Zhou, H. et al., "Peptide-siRNA nanocomplexes targeting NF-$_K$B subunit p65 suppress nascent experimental arthritis," The Journal of Clinical Investigation, Oct. 2014, pp. 4363-4374, vol. 124, No. 10.
Extended European Search Report dated Feb. 5, 2019 from related European Patent Application No. 16818881.1; 12 pgs.
Notice of Acceptance dated Mar. 19, 2018 from related Australian Patent Application No. 2014204012; 1 pg.
Office Action dated Feb. 27, 2018 from related Japanese Patent Application No. 2015-551782; 5 pgs.
Office Action dated Jul. 17, 2018 from related Japanese Patent Application No. 2015-551782; 3 pgs.
Office Action dated Aug. 14, 2018 from related Israeli Patent Application No. 239680; 8 pgs.
Office Action dated Nov. 6, 2018 from related Japanese Patent Application No. 2015-551782; 5 pgs.
Office Action dated Dec. 3, 2018 from related Mexican Patent Application No. MX/a/2015/008588; 3 pgs.
Tan, Y-X. et al., "Truncated peptides from melittin and its analog with high lytic activity at endosomal pH enhance branched polyethylenimine-mediated gene transfection," J. Gene Med., Apr. 2012, pp. 241-250, vol. 14, No. 4, John Wiley & Sons, Ltd.

SEQUENCE LISTING

<160> NUMBER OF SEQ ID NOS: 16

<210> SEQ ID NO 1
<211> LENGTH: 25
<212> TYPE: PRT
<213> ORGANISM: Artificial Sequence
<220> FEATURE:
<223> OTHER INFORMATION: SYNTHESIZED

<400> SEQUENCE: 1

Val Leu Thr Thr Gly Leu Pro Ala Leu Ile Ser Trp Ile Lys Arg Lys
1               5                   10                  15

Arg Gln His Arg Trp Arg Arg Arg Arg
            20                  25

<210> SEQ ID NO 2
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 2

Val Leu Thr Thr Gly Leu Pro Ala Leu Ile Ser Trp Ile Lys Arg Lys
1               5                   10                  15

Arg

<210> SEQ ID NO 3
<211> LENGTH: 18
<212> TYPE: PRT
<213> ORGANISM: Artificial Sequence
<220> FEATURE:
<223> OTHER INFORMATION: SYNTHESIZED

<400> SEQUENCE: 3

Val Leu Thr Thr Gly Leu Pro Ala Leu Ile Ser Trp Ile Lys Arg Lys
1               5                   10                  15

Arg Gln

<210> SEQ ID NO 4
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 4

Val Leu Thr Thr Gly Leu Pro Ala Leu Ile Ser Trp Ile Lys Arg Lys
1               5                   10                  15

Arg Gln His

<210> SEQ ID NO 5
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 5

Val Leu Thr Thr Gly Leu Pro Ala Leu Ile Ser Trp Ile Lys Arg Lys
1               5                   10                  15

Arg Gln His Arg
            20

<210> SEQ ID NO 6
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 6

Val Leu Thr Thr Gly Leu Pro Ala Leu Ile Ser Trp Ile Lys Arg Lys
1               5                   10                  15

Arg Gln His Arg Trp
            20

<210> SEQ ID NO 7
<211> LENGTH: 22
<212> TYPE: PRT
<213> ORGANISM: Artificial Sequence
<220> FEATURE:
<223> OTHER INFORMATION: SYNTHESIZED

<400> SEQUENCE: 7

Val Leu Thr Thr Gly Leu Pro Ala Leu Ile Ser Trp Ile Lys Arg Lys
1               5                   10                  15

Arg Gln His Arg Trp Arg
            20

<210> SEQ ID NO 8
<211> LENGTH: 23
<212> TYPE: PRT
<213> ORGANISM: Artificial Sequence
<220> FEATURE:
<223> OTHER INFORMATION: SYNTHESIZED

<400> SEQUENCE: 8

Val Leu Thr Thr Gly Leu Pro Ala Leu Ile Ser Trp Ile Lys Arg Lys
1               5                   10                  15

Arg Gln His Arg Trp Arg Arg
            20

<210> SEQ ID NO 9
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 9

Val Leu Thr Thr Gly Leu Pro Ala Leu Ile Ser Trp Ile Lys Arg Lys
1               5                   10                  15

Arg Gln His Arg Trp Arg Arg Arg
            20

<210> SEQ ID NO 10
<211> LENGTH: 25
<212> TYPE: PRT
<213> ORGANISM: Artificial Sequence
<220> FEATURE:
<223> OTHER INFORMATION: SYNTHESIZED

<400> SEQUENCE: 10

Val Leu Thr Thr Gly Leu Pro Ala Leu Ile Ser Trp Ile Lys Arg Lys
1               5                   10                  15

Arg Gln His Arg Trp Arg Arg Arg Arg
            20                  25

```
<210> SEQ ID NO 11
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 11

Val Leu Thr Thr Gly Leu Pro Ala Leu Ile Ser Trp Ile Arg Arg Arg
1               5                   10                  15

His Arg Arg His Cys
            20

<210> SEQ ID NO 12
<211> LENGTH: 25
<212> TYPE: PRT
<213> ORGANISM: Artificial Sequence
<220> FEATURE:
<223> OTHER INFORMATION: SYNTHESIZED

<400> SEQUENCE: 12

Val Leu Thr Thr Gly Leu Pro Ala Leu Ile Ser Trp Ile Lys Arg Lys
1               5                   10                  15

Arg Gln Gln Arg Trp Arg Arg Arg Arg
            20                  25

<210> SEQ ID NO 13
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 13

Val Leu Thr Thr Gly Leu Pro Ala Leu Ile Ser Trp Ile Lys Arg Lys
1               5                   10                  15

Arg Gln Gln Cys
            20

<210> SEQ ID NO 14
<211> LENGTH: 26
<212> TYPE: PRT
<213> ORGANISM: Artificial Sequence
<220> FEATURE:
<223> OTHER INFORMATION: SYNTHESIZED

<400> SEQUENCE: 14

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 15
<211> LENGTH: 19
<212> TYPE: RNA
<213> ORGANISM: Artificial Sequence
<220> FEATURE:
<223> OTHER INFORMATION: SYNTHESIZED

<400> SEQUENCE: 15
ggaguacccu gaagcuaua                                            19

<210> SEQ ID NO 16
```

```
<211> LENGTH: 19
<212> TYPE: RNA
<213> ORGANISM: Artificial Sequence
<220> FEATURE:
<223> OTHER INFORMATION: SYNTHESIZED

<400> SEQUENCE: 16
gaaagaagac agagccuau                                                    19
```

PEPTIDE-POLYNUCLEOTIDE COMPLEX FOR POLYNUCLEOTIDE TRANSFECTION

CROSS REFERENCE TO RELATED APPLICATIONS

This application is a national stage entry of PCT application No. PCT/US2016/040678, filed Jul. 1, 2016, which claims the benefit of U.S. provisional application No. 62/187,979, filed Jul. 2, 2015, each of which is hereby incorporated by reference in its entirety.

GOVERNMENTAL RIGHTS

This invention was made with government support under Grant Nos. U01 CA141541 and R01 HL073646-08 awarded by the National Institutes of Health (NIH). The government has certain rights in the invention.

FIELD OF THE INVENTION

The invention provides a peptide-polynucleotide complex that can be formulated as a pharmaceutical composition, and methods of use thereof.

BACKGROUND OF THE INVENTION

RNA interference (RNAi) with the use of small interfering RNA (siRNA) has been proposed as a highly effective therapy for myriad diseases including cancer and inflammatory diseases. However, despite nearly two decades of intense research, siRNA therapeutics have demonstrated limited success in translation to clinical applications due to poor cellular uptake and instability of free siRNA in serum. Cationic lipids and polymers have been successfully employed for siRNA transfection, but can exhibit unacceptable cytotoxicity and cause generation of reactive oxygen species (ROS) and $Ca^{+2}$ leakage. In addition, cell penetrating peptide (CPP) based siRNA transfection agents, although showing promise with respect to reducing cytotoxicity, have not achieved the high efficiency of traditional lipidic transfection agents due to lysosomal trapping.

Therefore, there is a need in the art for new classes of therapeutic siRNA compositions and siRNA transfection agents capable of efficient cellular uptake and delivery into the cytoplasm for treating diseases.

SUMMARY OF THE INVENTION

The present invention encompasses a pharmaceutical composition comprising a peptide-polynucleotide complex. The peptide-polynucleotide complex comprises a ratio of peptide:polynucleotide that is less than 50:1. The peptide is (a) non-lytic and capable of affecting the release of a polynucleotide from an endosome of a cell, and (b) comprises an amino acid sequence with at least 80% identity to the amino acid sequence of SEQ ID NO: 1. The polynucleotide is an RNA sequence or a DNA sequence. In an aspect, the peptide comprises at least one cationic region and at least one histidine residue located adjacent to at least one cationic region of the peptide. In another aspect, the polynucleotide is a non-coding RNA capable of regulating or inhibiting the expression of a nucleic acid sequence.

The present invention also encompasses a method of delivering a polynucleotide to the cytoplasm of a cell. The method comprises contacting a cell with a peptide-polynucleotide complex, the peptide-polynucleotide complex comprising a ratio of peptide:polynucleotide that is less than 50:1, wherein the peptide is (a) non-lytic and capable of affecting the release of a polynucleotide from an endosome of a cell, and (b) comprises an amino acid sequence with at least 80% identity to the amino acid sequence of SEQ ID NO: 1. In an aspect, the peptide comprises at least one cationic region and at least one histidine residue located adjacent to or within at least one cationic region of the peptide. In another aspect, the polynucleotide is a non-coding RNA capable of regulating or inhibiting the expression of a nucleic acid sequence.

The present invention also encompasses a method of delivering a polynucleotide to the cytoplasm of a cell in a subject in need thereof. The method comprises administering to the subject a therapeutically effective amount of a pharmaceutical composition comprising a peptide-polynucleotide complex, the peptide-polynucleotide complex comprising a ratio of peptide:polynucleotide that is less than a50:1, wherein the peptide is (a) non-lytic and capable of affecting the release of a polynucleotide from an endosome of a cell, and (b) comprises an amino acid sequence with at least 80% identity to the amino acid sequence of SEQ ID NO: 1. In an aspect, the peptide comprises at least one cationic region and at least one histidine residue located adjacent to or within at least one cationic region of the peptide. In another aspect, the polynucleotide is a non-coding RNA capable of regulating or inhibiting the expression of a nucleic acid sequence.

The present invention also encompasses an amino acid sequence that has at least 80% identity to SEQ ID NO: 1 and encodes a peptide that is non-lytic and capable of affecting the release of a polynucleotide from an endosome of a cell.

The present invention also encompasses a peptide comprising an amino acid sequence that has at least 80% identity to SEQ ID NO: 1, wherein the peptide is non-lytic and capable of affecting the release of a polynucleotide from an endosome of a cell.

Other aspects and iterations of the invention are described more thoroughly below.

DETAILED DESCRIPTION OF THE INVENTION

The present invention provides a peptide-polynucleotide complex capable of efficient transfection of the polynucleotide into the cytoplasm of a cell with reduced cytotoxicity, as compared to other methods of polynucleotide transfection known in the art. Advantageously, a peptide-polynucleotide complex of the invention is stable in the presence of serum and, therefore, is capable of efficiently delivering a polynucleotide to the cytoplasm of a cell in vivo. Accordingly, the present invention encompasses, a pharmaceutical composition comprising a peptide-polynucleotide complex of the invention, a method of preparing a peptide-polynucleotide complex of the invention, a method of using a peptide-polynucleotide complex of the invention to transfect the polynucleotide into the cytoplasm of a cell, and a kit for preparing a peptide-polynucleotide complex of the invention.

I. Peptide-Polynucleotide Complex

One aspect of the present invention encompasses a peptide-polynucleotide complex. A peptide-polynucleotide complex of the invention is capable of efficient transfection of a polynucleotide associated with the peptide into the cytoplasm of a cell. The peptide, the polynucleotide, the peptide-polynucleotide complex, and the cell are described below.

(a) Peptide

In an aspect, a peptide-polynucleotide complex of the invention comprises a peptide. In general, and as described in the examples, a peptide of the invention is derived from melittin and modified to attenuate its cytotoxicity while maintaining its propensity for interacting with membrane bilayers. Furthermore, the peptide is substantially non-lytic and non-cytotoxic to cells. Preferably, a peptide-polynucleotide complex of the invention comprises a peptide that (1) has a function substantially similar to a peptide with an amino acid sequence of SEQ ID NO: 1, and (2) has an amino acid sequence with similarity or identity to the amino acid sequence of SEQ ID NO: 1.

As used herein, the phrase "functions substantially similar to a peptide comprising SEQ ID NO: 1" refers to a substantially non-lytic and/or non-cytotoxic peptide that is capable of affecting the release of a polynucleotide from an endosome. In some embodiments a peptide of the invention is non-lytic. The term "non-lytic" means that the lipid bilayer of a cell typically is not compromised upon contact with the peptide. The integrity of the lipid bilayer may be assessed by the improper entry or exit of cellular or extracellular components into a cell. For example, cellular proteins and/or organelles may leak out of a cell with a compromised lipid bilayer. Alternatively, extracellular components (i.e., those that normally do not enter via gap junctions, for example) may enter a cell with a compromised lipid bilayer. It should be noted, however, that the peptide may penetrate the lipid bilayer of a cell and enter the interior of the cell, but in doing so the integrity of the lipid bilayer is not affected. In other embodiments, a peptide of the invention is substantially non-cytotoxic. The term "non-cytotoxic" indicates that the cell typically is not killed upon contact with the peptide. Typically, a peptide of the invention decreases cell viability by no more than about 10%, more preferably no more than about 7%, more preferably no more than about 5%, or more preferably no more than about 3%. In certain embodiments, a peptide of the invention is non-lytic and non-cytotoxic.

As described in Section I(b) and (c) below, a peptide of the invention is capable of associating with a polynucleotide. Thus, in one aspect, a peptide of the invention comprises at least one cationic region that interacts with a polynucleotide. Typically, a cationic region has 2 or more contiguous, basic amino acids. Importantly, a peptide of the invention also possesses an endosomolytic capacity, which allows it to affect the release of a polynucleotide from an endosome and into the cytoplasm of a cell. The term "endosomolytic" can be used to describe substances that initiate or facilitate the lysis of endosomes. As described in the Examples, protonation of histidine residues of a peptide of the invention promotes disassembly of the peptide-polynucleotide complex, which releases the peptide to permeabilize the endosomal membrane for polynucleotide release. Thus, in another aspect, a peptide of the invention comprises one or more histidine residues located adjacent to or within at least one cationic region of the peptide. By way of non-limiting example, if a peptide of the invention comprises three cationic regions, the peptide may have at least one histidine adjacent to or within the first cationic region of the peptide, at least one histidine adjacent to or within the second cationic region of the peptide, at least one histidine adjacent to or within the third cationic region of the peptide, at least one histidine adjacent to or within each of the first and second cationic region of the peptide, at least one histidine adjacent to or within each of the first and third cationic region of the peptide, at least one histidine adjacent to or within each of the second and third cationic region of the peptide, or at least one histidine adjacent to or within each of the first, second and third cationic region of the peptide. A histidine residue adjacent to a cationic region may be positioned before or after the cationic region. In some embodiments, a histidine residue adjacent to a cationic region is immediately adjacent to the region. In other embodiments, a histidine residue adjacent to a cationic region is not immediately adjacent to the region. For example, the histidine residue may be within about 2, 3, 4 or 5 positions from the cationic region. In other embodiments, a histidine residue is within a cationic region. The endosomolytic capacity of a peptide of the invention obviates the need for additional endosomolytic agents, such as chloroquine, fusogenic peptides, inactivated adenoviruses and polyethyleneimine, for releasing transfected polynucleotides from endosomes for delivery into the cytoplasm of a cell. Such known endosomolytic agents have negative effects on cells, and may increase cytotoxicity during transfection.

In some embodiments, a peptide of the invention comprises SEQ ID NO: 1. In other embodiments, a peptide of the inventions consists of SEQ ID NO: 1. In certain embodiments, a peptide of the invention is a variant of SEQ ID NO: 1, wherein the variant comprises at least 10 contiguous amino acids of SEQ ID NO: 1 and functions substantially similar to a peptide comprising SEQ ID NO: 1. For instance, a peptide of the invention may encompass at least 10, 11, 12, 13, 14, 15, 16, 17, 18, 19, or 20 contiguous amino acids of SEQ ID NO: 1. In some embodiments, a peptide of the invention is chosen from Table A.

TABLE A

| SEQ ID NO. | Sequence |
|---|---|
| 1 | VLTTGLPALISWIKRKRQHRWRRRR |
| 2 | VLTTGLPALISWIKRKR |
| 3 | VLTTGLPALISWIKRKRQ |
| 4 | VLTTGLPALISWIKRKRQH |
| 5 | VLTTGLPALISWIKRKRQHR |
| 6 | VLTTGLPALISWIKRKRQHRW |
| 7 | VLTTGLPALISWIKRKRQHRWR |
| 8 | VLTTGLPALISWIKRKRQHRWRR |
| 9 | VLTTGLPALISWIKRKRQHRWRRR |
| 10 | VLTTGLPALISWIKRKRQHRWRRRR |

In a preferred embodiment, a peptide of the invention comprises an amino acid sequence that has at least 80% identity to SEQ ID NO: 1, wherein the peptide is non-lytic and is capable of affecting the release of a polynucleotide from an endosome of a cell. The peptide comprising an amino acid sequence that has at least 80% identity to SEQ ID NO: 1, can have about 80%, preferably about 85%, more preferably about 90%, more preferably about 95% identity to the amino acid sequence of SEQ ID NO: 1. A peptide of the invention comprising an amino acid sequence that has at least 80% identity to SEQ ID NO: 1 may comprise one or more amino acids that have been conservatively substituted. For instance, one, two, three, four, five, six, seven, eight, nine, or more than nine amino acids may be conservatively substituted as long as the resulting peptide functions substantially similar to a peptide comprising SEQ ID NO: 1.

In another aspect, the present invention provides an amino acid sequence that has at least 80% identity to SEQ ID NO: 1 and encodes a peptide that is non-lytic and capable of affecting the release of a polynucleotide from an endosome of a cell. In some embodiments, the amino acid sequence has at least 80% identity, at least 85% identity, at least 90% identity, or at least 95% identity to SEQ ID NO: 1. In other embodiments, the amino acid sequence is SEQ ID NO: 1.

A peptide of the invention may be produced using a variety of techniques known in the art. The peptides may be isolated using standard techniques, may be synthesized using standard techniques, or may be purchased or obtained from a depository.

When a peptide of the invention contains a C-terminal thiol in the form of a cysteine residue, a peptide of the invention may be able to form a disulfide bond with another free thiol group, for example, with a free thiol group from the same or different peptide. A skilled artisan can readily determine whether dimer formation does or does not improve the delivery of plasmid DNA. Without wishing to be bound by theory, dimer formation may improve the delivery of plasmid DNA for certain peptides of the invention due to improved DNA condensation. Dimerization may be induced by incubation of free peptide in 20% DMSO for 24-72 hours, or by other methods known in other art. As a non-limiting example, free thiols may be quantified by colorimetric assays using Ellman's Reagent.

A peptide of the invention may be labeled. Non-limiting examples of suitable labels include fluorescent labels, chemiluminescent labels, radioactive labels, colorimetric labels, and resonance labels. Methods of labeling peptides are well known in the art.

A peptide may be bound to a cargo complex. As used herein, the term "cargo complex" may refer to any molecule or agent that may be carried by or bound to the peptide other than a polynucleotide of the invention. Stated another way, a peptide of the invention may be bound to a cargo complex in addition to a polynucleotide of the invention. For instance, a cargo complex may be an imaging cargo, a therapeutic cargo, a cytotoxic cargo, or a targeting cargo.

Non-limiting examples of imaging cargo molecules and agents may include any molecule, agent, or material having a detectable physical or chemical property. Such imaging cargos have been well-developed in the field of fluorescent imaging, magnetic resonance imaging, positron emission tomography, Raman imaging, optical coherence tomography, photoacoustic imaging, Fourier transform infrared imaging, or immunoassays and, in general, most any label useful in such methods may be applied to the present invention. For a review of various labeling or signal producing systems that may be used, see U.S. Pat. No. 4,391,904, incorporated herein by reference in its entirety.

Non-limiting examples of therapeutic cargo may include any substance that has a biological activity, such as pharmacological agents. Such therapeutic cargo may include analgesics, antipyretics, antiasthmatics, antibiotics, antidepressants, antidiabetics, antifungal agents, antihypertensive agents, anti-inflammatories including non-steroidal and steroidal, antineoplastics, antianxiety agents, immunosuppressive agents, antimigraine agents, sedatives, hypnotics, anti-anginal agents, antipsychotic agents, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines, anti-restenosis agents, antipruritics, agents useful for calcium regulation, antibacterial agents, antiviral agents, antimicrobials, anti-infectives, bronchodilators, steroidal compounds and hormones, and combinations thereof. Alternatively, a cargo complex may be in the form of components of molecular complexes or pharmacologically acceptable salts.

Cytotoxic cargo refers to a molecule or agent that is detrimental to (e.g., kills or damages) a cell. Examples may include anti-microtubule drugs such as the taxols (paclitaxel, docetaxel) and vinca alkaloids (vincristine, vinblastine). For instance, examples may include taxol, cytochalasin B, gramicidin D, ethidium bromide, emetine, mitomycin, etoposide, tenoposide, vincristine, vinblastine, colchicin, doxorubicin, daunorubicin, dihydroxy anthracin didne, mitoxantrone, mithramycin, actinomycin D, 1-dehydrotestosterone, glucocorticoids, procaine, tetracaine, lidocaine, propranolol, and puromycin and analogs or homologs thereof.

A targeting cargo may be any molecule or agent that directs a peptide-polynucleotide complex of the invention to a cell. A targeting cargo may be directed to a eukaryotic target cell or a prokaryotic target cell. Non-limiting examples of targeting agents may include an antibody or an antibody fragment, a receptor ligand, a small molecule, a peptide, a polypeptide, a lipid, a carbohydrate, a nucleic acid, a siRNA, a shRNA, an antisense RNA, a dendrimer, a microbubble, or an aptamer.

The means by which a cargo complex is bound to a peptide of the invention can and will vary depending on the embodiment. A cargo complex may be bound to a peptide of the invention by any means known in the art, including covalently or non-covalently.

(b) Polynucleotide

In another aspect, a peptide-polynucleotide complex of the invention comprises a polynucleotide. A polynucleotide may be single stranded, double stranded, or a combination thereof. In some embodiments, a polynucleotide is double stranded. In other embodiments, a polynucleotide is single stranded. In yet other embodiments, a polynucleotide is a combination of single stranded and double stranded.

A polynucleotide of the invention may comprise a ribonucleic acid (RNA), a deoxyribonucleic acid (DNA), or a combination of RNA and DNA. Additionally, a polynucleotide may comprise modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). Alternatively, a polynucleotide may be a nucleotide mimic. Examples of nucleotide mimics include locked nucleic acids (LNA), peptide nucleic acids (PNA), and phosphorodiamidate morpholino oligomers (PMO).

In some embodiments, a polynucleotide of the invention is a combination of RNA and DNA. In other embodiments, a polynucleotide comprises DNA. When a polynucleotide is DNA, the polynucleotide may comprise an expression cassette. As used herein, an "expression cassette" is a nucleic acid construct comprising a nucleic acid sequence encoding a protein or peptide operably linked to a promoter. In certain embodiments, a nucleic acid construct further comprises additional regulatory sequences. A non-limiting example of an additional regulatory sequence includes a transcription termination sequence. Other additional regulatory sequences are known in the art. As used herein, the term promoter may mean a synthetic or naturally-derived molecule capable of conferring or activating expression of a target nucleic acid sequence in a cell. A promoter may be the promoter normally associated with a DNA polynucleotide of the invention, or may be a heterologous promoter. A heterologous promoter may be derived from such sources as viruses, bacteria, fungi, plants, insects, and animals. A promoter may regulate the expression of a DNA sequence constitutively or differentially with respect to the cell, the tissue or organ in which expression occurs. Or, a promoter may regulate expression with respect to developmental stage, or in response to external stimuli such as physiological stresses, pathogens, metal ions, or inducing agents or activators (i.e. an inducible promoter). Non-limiting representative examples of promoters may include the bacteriophage T7 promoter, bacteriophage T3 promoter, SP6 promoter, HSP70 basal promoter, lac operator-promoter, tac promoter, SV40 late promoter, SV40 early promoter, RSV-LTR promoter, CMV IE promoter, a promoter comprising the tetracycline response element (TRE) nucleic acid sequence, and the CMV IE promoter. In some alternatives of these embodiments, a DNA polynucleotide of the invention is incorporated into a vector. One of skill in the art would be able to construct a vector through standard recombinant techniques (see, for example, Sambrook et al., 2001 and Ausubel et al., 1996, both incorporated herein by reference). Vectors include but are not limited to plasmids, cosmids, transposable elements, viruses (bacteriophage, animal viruses, and plant viruses), and artificial chromosomes (e.g., YACs), such as retroviral vectors (e.g., derived from Moloney murine leukemia virus vectors (MoMLV), MSCV, SFFV, MPSV, SNV etc.), lentiviral vectors (e.g., derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, and Rous sarcoma virus vectors.

In yet other embodiments, a polynucleotide comprises RNA. Non-limiting examples of RNA sequences may include mRNA capable of encoding a protein, and non-coding RNA such as tRNA, rRNA, snoRNAs, microRNAs, siRNAs, piRNAs and the long noncoding RNA (lncRNA). For instance, a nucleic acid may comprise mRNA. In preferred embodiments, when a nucleic acid comprises mRNA, the mRNA molecule may be 5' capped, polyadenylated, or capped and polyadenylated. Alternatively, a mRNA molecule may comprise an internal ribosomal entry sites (IRES) for translation of an internal open reading frame of the mRNA.

In certain embodiments, a polynucleotide comprises non-coding RNA capable of regulating or inhibiting the expression of a nucleic acid sequence expressed in a cell. Non-limiting examples of non-coding RNA capable of regulating or inhibiting the expression of a nucleic acid sequence expressed in a cell include microRNAs (also known as miRNAs), siRNAs, piRNAs and lncRNAs. In general, transfection of a cell with a non-coding RNA capable of regulating or inhibiting the expression of a nucleic acid sequence may lead to cleavage of the nucleic acid sequence, may enhance, prevent, or disrupt translation of the nucleic acid sequence into a protein, or may regulate the transcription of a nucleic acid sequence.

In preferred embodiments, a polynucleotide of the invention comprises a non-coding RNA capable of disrupting expression of a nucleic acid sequence expressed in a cell. As used herein, "disrupting expression of a nucleic acid sequence" may be used to describe any decrease in the expression level of a nucleic acid sequence, or a protein translated from the nucleic acid sequence, when compared to a level of expression of the nucleic acid sequence in a cell that was not treated with a peptide-polynucleotide complex of the invention. In some alternatives of the embodiments, a polynucleotide comprises a short interfering RNA (siRNA).

In a preferred embodiment, a polynucleotide of the invention comprises a non-coding RNA capable of disrupting the expression of a nucleic acid sequence encoding STAT3. In another preferred embodiment, a polynucleotide of the invention comprises a non-coding RNA capable of disrupting the expression of a nucleic acid sequence encoding JNK2. In certain preferred embodiments, the non-coding RNA is an siRNA. In other preferred embodiments, the non-coding RNA is a miRNA. In still other preferred embodiments, the non-coding RNA is a shRNA.

In yet another preferred embodiment, a polynucleotide of the invention comprises a non-coding RNA capable of disrupting the expression of a nucleic acid sequence normally associated with a NFκB signaling pathway. Non-limiting examples of a NFκB pathway may include the canonical NFκB pathway and the non-canonical NFκB pathway. In certain preferred embodiments, the non-coding RNA is an siRNA. In other preferred embodiments, the non-coding RNA is a miRNA. In still other preferred embodiments, the non-coding RNA is a shRNA.

Non-limiting examples of a nucleic acid sequence normally associated with the canonical NFκB signaling pathway may include a nucleic acid encoding the transcription factor p65 subunit of the canonical NFκB signaling pathway and a nucleic acid encoding the transcription factor p105/p50 subunit of the canonical NFκB signaling pathway. In one alternative of the embodiments, a polynucleotide of the invention comprises a non-coding RNA capable of disrupting the expression of a nucleic acid sequence encoding the p105/p50 subunit of the canonical NFκB signaling pathway. In another alternative of the embodiments, a polynucleotide of the invention comprises a non-coding RNA capable of disrupting the expression of a nucleic acid sequence encoding the p65 subunit of the canonical NFκB signaling pathway. In an exemplary embodiment, a polynucleotide of the invention comprises a siRNA with a nucleic acid sequence of SEQ ID NO: 15 (GGAGUACCCUGAAGCUAUA).

Non-limiting examples of a nucleic acid sequence normally associated with the canonical NFκB signaling pathway may include a nucleic acid encoding the p100/p52 subunit of the non-canonical NFκB signaling pathway and a nucleic acid encoding the RelB subunit of the non-canonical NFκB signaling pathway. In one alternative of the embodiments, a polynucleotide of the invention comprises a non-coding RNA capable of disrupting the expression of a nucleic acid sequence encoding the RelB subunit of the non-canonical NFκB signaling pathway. In another alternative of the embodiments, a polynucleotide of the invention comprises a non-coding RNA capable of disrupting the expression of a nucleic acid sequence encoding the p100/p52 subunit of the non-canonical NFκB signaling pathway. In an exemplary embodiment, a polynucleotide of the invention comprises a siRNA with a nucleic acid sequence of SEQ ID NO: 16 (GAAAGAAGACAGAGCCUAU).

In some embodiments, a polynucleotide of the invention comprises more than one non-coding RNA capable of disrupting the expression of a nucleic acid sequence normally associated with a NFκB signaling pathway. In preferred embodiments, a polynucleotide of the invention comprises a non-coding RNA capable of disrupting the expression of a nucleic acid sequence normally associated with the canonical NFκB signaling pathway, and a non-coding RNA capable of disrupting the expression of a nucleic acid sequence normally associated with the non-canonical NFκB signaling pathway. In an exemplary embodiment, a polynucleotide of the invention comprises a non-coding RNA capable of disrupting the expression of a nucleic acid sequence encoding the p65 subunit of the canonical NFκB signaling pathway, and a non-coding RNA capable of disrupting the expression of a nucleic acid sequence encoding the p100/p52 subunit of the canonical NFκB signaling pathway.

In general, a siRNA comprises a double-stranded RNA molecule that ranges from about 15 to about 29 nucleotides in length. In some embodiments, the siRNA may be 16, 17, 18, 19, 20, 21, 22, 23, 24, 25, 26, 27, 28 or 29 nucleotides in length. In other embodiments, the siRNA may be about 16 to about 18, about 17 to about 19, about 21 to about 23, about 24 to about 27, or about 27 to about 29 nucleotides in length. In a preferred embodiment, the siRNA may be about 21 nucleotides in length. A siRNA may optionally further comprise one or two single-stranded overhangs, e.g., a 5' overhang on one or both ends, a 3' overhang on one or both ends, or a combination thereof. The siRNA may be formed from two RNA molecules that hybridize together or, alternatively, may be generated from a short hairpin RNA (shRNA) (see below). In some embodiments, the two strands of the siRNA may be completely complementary, such that no mismatches or bulges exist in the duplex formed between the two sequences. In other embodiments, the two strands of the siRNA may be substantially complementary, such that one or more mismatches and/or bulges may exist in the duplex formed between the two sequences. In certain embodiments, one or both of the 5' ends of the siRNA may have a phosphate group, while in other embodiments one or both of the 5' ends lack a phosphate group. In other embodiments, one or both of the 3' ends of the siRNA may have a hydroxyl group, while in other embodiments one or both of the 5' ends lack a hydroxyl group.

One strand of the siRNA, which is referred to as the "antisense strand" or "guide strand," includes a portion that hybridizes with a target transcript. A target transcript refers to a nucleic acid sequence expressed by a cell for which it is desired expression be disrupted. In the context of a therapeutic composition of the invention, disrupting expression of a target transcript may produce a beneficial effect. In preferred embodiments, the antisense strand of the siRNA may be completely complementary with a region of the target transcript, i.e., it hybridizes to the target transcript without a single mismatch or bulge over a target region between about 15 and about 29 nucleotides in length, preferably at least 16 nucleotides in length, and more preferably about 18-20 nucleotides in length. In other embodiments, the antisense strand may be substantially complementary to the target region, i.e., one or more mismatches and/or bulges may exist in the duplex formed by the antisense strand and the target transcript. Typically, siRNAs are targeted to exonic sequences of the target transcript. Those of skill in the art are familiar with programs, algorithms, and/or commercial services that design siRNAs for target transcripts. An exemplary example is the Rosetta siRNA Design Algorithm (Rosetta Inpharmatics, North Seattle, Wash.), MISSION® siRNA (Sigma-Aldrich, St. Louis, Mo.) and siGENOME siRNA (Thermo Scientific). The siRNA may be enzymatically synthesized in vitro using methods well known to those of skill in the art. Alternatively, the siRNA may be chemically synthesized using oligonucleotide synthesis techniques that are well known in the art.

In other embodiments, the non-coding RNA may be a short hairpin RNA (shRNA). In general, a shRNA is an RNA molecule comprising at least two complementary portions that are hybridized or are capable of hybridizing to form a double-stranded structure sufficiently long to mediate RNA interference (as described above), and at least one single-stranded portion that forms a loop connecting the regions of the shRNA that form the duplex. The structure may also be called a stem-loop structure, with the stem being the duplex portion. In some embodiments, the duplex portion of the structure may be completely complementary, such that no mismatches or bulges exist in the duplex region of the shRNA. In other embodiments, the duplex portion of the structure may be substantially complementary, such that one or more mismatches and/or bulges may exist in the duplex portion of the shRNA. The loop of the structure may be from about 1 to about 20 nucleotides in length, preferably from about 4 to about 10 about nucleotides in length, and more preferably from about 6 to about 9 nucleotides in length. The loop may be located at either the 5' or 3' end of the region that is complementary to the target transcript (i.e., the antisense portion of the shRNA).

The shRNA may further comprise an overhang on the 5' or 3' end. The optional overhang may be from about 1 to about 20 nucleotides in length, and more preferably from about 2 to about 15 nucleotides in length. In some embodiments, the overhang may comprise one or more U residues, e.g., between about 1 and about 5 U residues. In some embodiments, the 5' end of the shRNA may have a phosphate group, while in other embodiments it may not. In other embodiments, the 3' end of the shRNA may have a hydroxyl group, while in other embodiments it may not. In general, shRNAs are processed into siRNAs by the conserved cellular RNAi machinery. Thus, shRNAs are precursors of siRNAs and are similarly capable of inhibiting expression of a target transcript that is complementary of a portion of the shRNA (i.e., the antisense portion of the shRNA). Those of skill in the art are familiar with the available resources (as detailed above) for the design and synthesis of shRNAs. An exemplary example is MISSION® shRNAs (Sigma-Aldrich).

In still other embodiments, the non-coding RNA may be an RNA interference (RNAi) RNA expression vector. Typically, an RNAi expression vector may be used for intracellular (in vivo) synthesis of RNAi agents, such as miRNAs, siRNAs or shRNAs. In one embodiment, two separate, complementary siRNA strands may be transcribed using a single vector containing two promoters, each of which directs transcription of a single siRNA strand (i.e., each promoter is operably linked to a template for the siRNA so that transcription may occur). The two promoters may be in the same orientation, in which case each is operably linked to a template for one of the complementary siRNA strands. Alternatively, the two promoters may be in opposite orientations, flanking a single template so that transcription for the promoters results in synthesis of two complementary siRNA strands. In another embodiment, the RNAi expression vector may contain a promoter that drives transcription of a single RNA molecule comprising two complementary regions, such that the transcript forms a shRNA.

Generally speaking, the promoters utilized to direct in vivo expression of the one or more siRNA or shRNA transcription units may be promoters for RNA polymerase III (Pol III). Certain Pol III promoters, such as U6 or H1 promoters, do not require cis-acting regulatory elements within the transcribed region, and thus, are preferred in certain embodiments. In other embodiments, promoters for Pol II may be used to drive expression of the one or more siRNA or shRNA transcription units. In some embodiments, tissue-specific, cell-specific, or inducible Pol II promoters may be used.

A construct that provides a template for the synthesis of siRNA or shRNA may be produced using standard recombinant DNA methods and inserted into any of a wide variety of different vectors suitable for expression in eukaryotic cells. Guidance may be found in Current Protocols in Molecular Biology (Ausubel et al., John Wiley & Sons, New York, 2003) or Molecular Cloning: A Laboratory Manual (Sambrook & Russell, Cold Spring Harbor Press, Cold Spring Harbor, N.Y., 3rd edition, 2001). Those of skill in the art also appreciate that vectors may comprise additional regulatory sequences (e.g., termination sequence, translational control sequence, etc.), as well as selectable marker sequences. DNA plasmids are known in the art, including those based on pBR322, PUC, and so forth. Since many expression vectors already contain a suitable promoter or promoters, it may only be necessary to insert the nucleic acid sequence that encodes the RNAi agent of interest at an appropriate location with respect to the promoter(s). Viral vectors may also be used to provide intracellular expression of RNAi agents. Suitable viral vectors include retroviral vectors, lentiviral vectors, adenoviral vectors, adeno-associated virus vectors, herpes virus vectors, and so forth. In preferred embodiments, the RNAi expression vector is a shRNA lentiviral-based vector or lentiviral particle, such as that provided in MISSION® TRC shRNA products (Sigma-Aldrich).

Nucleic acid sequences of the invention may be obtained using a variety of different techniques known in the art. The nucleotide sequences, as well as homologous sequences, may be isolated using standard techniques, purchased or obtained from a depository. Once the nucleotide sequence is obtained, it may be amplified for use in a variety of applications, using methods known in the art.

(c) Polypeptide-Polynucleotide Complex

In another aspect of the invention, a polypeptide and a polynucleotide of the invention associate to form a complex. As used herein, the term "associate" may refer to the interaction of a peptide and a polynucleotide through non-covalent bonds, or to the covalent bonding of a peptide and a polynucleotide. In preferred embodiments, a polypeptide and a polynucleotide of the invention associate through non-covalent bonds such as a hydrogen bond, an ionic bond, a bond based on Van der Waals, a hydrophobic bond, or electrostatic interactions. For instance, a peptide of the invention may have an overall net positive charge, which may allow the peptide to associate with a polynucleotide of the invention through electrostatic interactions to form a complex of the invention. Methods for forming a polypeptide-polynucleotide complex of the invention are known in the art and further described in Section V and in the Examples.

The molar ratio of peptide to polynucleotide at which a peptide of the invention associates with a polynucleotide of the invention can and will vary depending on the peptide, the polynucleotide composition, or the size of the polynucleotide, and may be determined experimentally. In essence, a suitable molar ratio of a peptide of the invention to a polynucleotide of the invention may be a molar ratio wherein the peptide completely complexes the polynucleotide, while minimizing exposure of a subject to the peptide. In the present invention, the ratio is less than 50:1 peptide:polynucleotide.

For instance, a peptide of the invention may associate with a polynucleotide in a peptide to polynucleotide molar ratio of about 1:1, 5:1, 10:1, 15:1, 20:1, 25:1, 30:1, 35:1, 40:1, or about 45:1. In some embodiments, a peptide and a polynucleotide of the invention associate in a peptide to polynucleotide molar ratio of about 1:1, 5:1, 10:1, 15:1, 20:1, 25:1, 30:1, 35:1, 40:1, or about 45:1 In other embodiments, a peptide of the invention and a polynucleotide of the invention may associate in a peptide to polynucleotide molar ratio of about 5:1 to about 45:1. In other embodiments, a peptide of the invention and a polynucleotide of the invention may associate in a peptide to polynucleotide molar ratio of about 5:1 to about 35:1, about 10:1 to about 40:1, or about 15:1 to about 45:1. In other embodiments, a peptide of the invention and a polynucleotide of the invention may associate in a peptide to polynucleotide molar ratio of about 5:1 to about 30:1, about 10:1 to about 35:1, about 15:1 to about 40:1, or about 20:1 to about 45:1. In other embodiments, a peptide of the invention and a polynucleotide of the invention may associate in a peptide to polynucleotide molar ratio of about 5:1 to about 25:1, about 10:1 to about 30:1, about 15:1 to about 35:1, or about 20:1 to about 40:1, or about 25:1 to about 45:1.

When a polynucleotide of the invention is siRNA, a suitable molar ratio of a peptide of the invention to a polynucleotide of the invention capable of completely complexing the siRNA polynucleotide is less than 50:1. Stated another way, in some embodiments, a molar ratio of a peptide and a siRNA polynucleotide of the invention may be between about 5:1 to about 45:1. In other embodiments, a molar ratio of a peptide and a siRNA polynucleotide of the invention may be about 5:1, about 6:1, about 7:1, about 8:1, about 9:1, about 10:1, about 11:1, about 12:1, about 13:1, about 14:1, or about 15:1. In other embodiments, a molar ratio of a peptide and a siRNA polynucleotide of the invention may be about 10:1, about 11:1, about 12:1, about 13:1, about 14:1, about 15:1, about 16:1, about 17:1, about 18:1, about 19:1, or about 20:1. In yet other embodiments, a molar ratio of a peptide and a siRNA polynucleotide of the invention may be about 15:1, about 16:1, about 17:1, about 18:1, about 19:1, about 20:1, about 21:1, about 22:1, about 23:1, about 24:1, or about 25:1. In still other embodiments, a molar ratio of a peptide and a siRNA polynucleotide of the invention may be about 20:1, about 21:1, about 22:1, about 23:1, about 24:1, about 25:1, about 26:1, about 27:1, about 28:1, about 29:1, about 30:1, 31:1, about 32:1, about 33:1, about 34:1, or about 35:1. In other embodiments, a molar ratio of a peptide and a siRNA polynucleotide of the invention may be about 25:1, about 26:1, about 27:1, about 28:1, about 29:1, about 30:1, about 31:1, about 32:1, about 33:1, about 34:1, or about 35:1. In other embodiments, a molar ratio of a peptide and a siRNA polynucleotide of the invention may be about 30:1, about 31:1, about 32:1, about 33:1, about 34:1, about 35:1, about 36:1, about 37:1, about 38:1, about 39:1, or about 40:1. In other embodiments, a molar ratio of a peptide and a siRNA polynucleotide of the invention may be about 35:1, about 36:1, about 37:1, about 38:1, about 39:1, or about 40:1, about 41:1, about 42:1, about 43:1, about 44:1, about 45:1, about 46:1, about 47:1, about 48:1, or about 49:1.

Methods of determining a molar ratio wherein the peptide is capable of completely complexing the polynucleotide are known in the art, and may include gel retardation assays as described in the examples. Methods of determining a molar ratio wherein exposure of a subject to the peptide is minimized are known in the art, and may include cytotoxicity measurements using increasing doses of the polypeptide.

A peptide-polynucleotide complex of the invention may be about 50 nm to about 999 nm in diameter, more preferably about 50 nm to about 500 nm in diameter, more preferably about 50 nm to about 250 nm in diameter. As such, a peptide-polynucleotide complex of the invention may be referred to as a "nanoparticle". In some embodiments, a nanoparticle of the invention is about 50, 55, 60, 65, 70, 75, 80, 85, 90, 95, 100, 105, 110, 115, or about 120 nm in diameter. In other embodiments, a nanoparticle of the invention is about 125, 130, 135, 140, 145, 150, 155, 160, 165, 170, 175, 180, 185, 190, 195, 200, 205, 210, 215, or 220 nm in diameter. In other embodiments, a nanoparticle of the invention is about 225, 230, 235, 240, 245, 250, 255, 260, 265, or 270 nm in diameter. In other embodiments, a nanoparticle of the invention is about 280, 285, 290, 295, 300, 310, 315, 320, 325, 330, 335, 340, or 345 nm in diameter. In other embodiments, a nanoparticle of the invention is about 350, 355, 360, 370, 375, 380, 385, 390, 395, 400, 405, 410, or 415 nm in diameter. In other embodiments, a nanoparticle of the invention is about 420, 425, 430, 435, 440, 445, 450, 455, 460, 465, 470, 475, 480, 485, 490, 495, or 500 nm in diameter. In other embodiments, a nanoparticle of the invention is about 570, 575, 580, 585, 590, 595, 600, 605, 610, 615, 620, 625, or 630 nm in diameter.

In a preferred embodiment, a nanoparticle of the invention is about 50 to about 250 nm in diameter. For example, a nanoparticle of the invention may be about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120, about 121, about 122, about 123, about 124, about 125, about 126, about 127, about 128, about 129, about 130, about 131, about 132, about 133, about 134, about 135, about 136, about 137, about 138, about 139, about 140, about 141, about 142, about 143, about 144, about 145, about 146, about 147, about 148, about 149, about 150, about 151, about 152, about 153, about 154, about 155, about 156, about 157, about 158, about 159, about 160, about 161, about 162, about 163, about 164, about 165, about 166, about 167, about 168, about 169, about 170, about 171, about 172, about 173, about 174, about 175, about 176, about 177, about 178, about 179, about 180, about 181, about 182, about 183, about 184, about 185, about 186, about 187, about 188, about 189, about 190, about 191, about 192, about 193, about 194, about 195, about 196, about 197, about 198, about 199, about 200, about 201, about 202, about 203, about 204, about 205, about 206, about 207, about 208, about 209, about 210, about 211, about 212, about 213, about 214, about 215, about 216, about 217, about 218, about 219, about 220, about 221, about 222, about 223, about 224, about 225, about 226, about 227, about 228, about 229, about 230, about 231, about 232, about 233, about 234, about 235, about 236, about 237, about 238, about 239, about 240, about 241, about 242, about 243, about 244, about 245, about 246, about 247, about 248, about 249, or about 250 nm in diameter. In another preferred embodiment, a nanoparticle of the invention is about 50 to about 200 nm in diameter. In another preferred embodiment, a nanoparticle of the invention is about 50 to about 150 nm in diameter. In another preferred embodiment, a nanoparticle of the invention is about 50 to about 100 nm in diameter. In another preferred embodiment, a nanoparticle of the invention is about 75 to about 125 nm in diameter. In another preferred embodiment, a nanoparticle of the invention is about 100 to about 150 nm in diameter. In another preferred embodiment, a nanoparticle of the invention is about 125 to about 175 nm in diameter. In another preferred embodiment, a nanoparticle of the invention is about 150 to about 200 nm in diameter. In another preferred embodiment, a nanoparticle of the invention is about 175 to about 225 nm in diameter. In another preferred embodiment, a nanoparticle of the invention is about 200 to about 250 nm in diameter. In another preferred embodiment, a nanoparticle of the invention is about 180 to about 200 nm in diameter.

In certain embodiments, a nanoparticle comprising a peptide-polynucleotide complex of the invention may comprise an aggregate of smaller particles of about 5 to about 30 nm in diameter. As such, a nanoparticle of the invention may comprise an aggregate of smaller particles of about 5, 6, 7, 8, 9, 10, 11, 12, 13, 14, 15, 16, 17, 18, 19, 20, 21, 22, 23, 24, 25, 26, 27, 28, 29, or about 30 nm in diameter. In some embodiments, a nanoparticle comprising a peptide-polynucleotide complex of the invention comprises an aggregate of smaller particles of about 5, 6, 7, 8, 9, 10, 11, 12, 13, 14, or about 15 nm in diameter. In other embodiments, a nanoparticle comprising a peptide-polynucleotide complex of the invention comprises an aggregate of smaller particles of about 10, 11, 12, 13, 14, 15, 16, 17, 18, 19, or about 20 nm in diameter. In yet other embodiments, a nanoparticle comprising a peptide-polynucleotide complex of the invention comprises an aggregate of smaller particles of about 15, 16, 17, 18, 19, 20, 21, 22, 23, 24, or about 25 nm in diameter. In other embodiments, a nanoparticle comprising a peptide-polynucleotide complex of the invention comprises an aggregate of smaller particles of about 20, 21, 22, 23, 24, 25, 26, 27, 28, 29, or about 30 nm in diameter.

A nanoparticle of the invention may be further modified to enhance stability of the nanoparticle. For instance, a nanoparticle of the invention may be coated with albumin to enhance stability. A nanoparticle of the invention coated with albumin may be about 5 to about 90 nm or more in diameter. As such, a nanoparticle of the invention may comprise particles of about 5, about 10, about 15, about 20, about 25, about 30, about 35, about 40, about 45, about 50, about 55, about 60, about 65, about 70, about 75, about 80, about 85, about or about 90 nm in diameter. In some embodiments, a nanoparticle of the invention comprises particles of about 5, about 10, about 15, about 20, about 25, or about 30 nm in diameter. In other embodiments, a nanoparticle of the invention comprises particles of about 30, about 35, about 40, about 45, about 50, or about 55 nm in diameter. In yet other embodiments, a nanoparticle of the invention comprises particles of about 55, about 60, about 65, about 70, about 75, or about 80 nm in diameter. In other embodiments, a nanoparticle of the invention comprises particles of about 80, about 85, or about 90 nm or more in diameter. In preferred embodiments, a nanoparticle of the invention comprises particles of about 35, about 40, about 45, about 50, about 55, about 60, about 65, about 70, or about 75 nm in diameter.

Particle size may be assessed using methods known in the art. Non-limiting examples of methods of measuring the size of a particle may include dynamic light scattering, laser diffraction, electrozone (electric sensing zone), light obscuration—also referred to as photozone and single particle optical sensing (SPOS), sieve analysis, aerodynamic measurements, air permeability diameter, sedimentation, measuring the zeta potential of the particle, or combinations thereof. In a preferred embodiment, particle size is assessed by dynamic light scattering. In another preferred embodiment, particle size is assessed by measuring the zeta potential of the particle. In yet another preferred embodiment, particle size is assessed by dynamic light scattering or by measuring the zeta potential of the particle.

A nanoparticle of the invention may have a zeta potential of about −15 to about 20 mV, preferably about 0 mV or more. For instance, a nanoparticle may have a zeta potential of about 1, about 2, about 3, about 4, about 5, about 6, about 7, about 8, about 9, about 10, about 11, about 12, about 13, about 14, about 15, about 16, about 17, about 18, about 19 or about 20 mV or more. In some embodiments, a nanoparticle has a zeta potential of about 1, about 2, about 3, about 4, or about 5 mV. In other embodiments, a nanoparticle has a zeta potential of about 10, 11, 12, 13, or about 14 mV. In yet other embodiments, a nanoparticle has a zeta potential of about 11, about 12, about 13, about 14, or about 15 mV. In an exemplary embodiment, a nanoparticle has a zeta potential of about 1, about 2, about 3, about 4, or about 5 mV. In other embodiments, a nanoparticle has a zeta potential of about 10, about 11, 12, about 13, or about 14 mV. In an exemplary embodiment, a nanoparticle has a zeta potential of about 3.72 mV. In another exemplary embodiment, a nanoparticle has a zeta potential of about 12 mV. In yet another exemplary embodiment, a nanoparticle has a zeta potential of about 13.1 mV.

A nanoparticle comprising a peptide-polynucleotide complex of the invention may have a positive to negative charge ratio of about 1:1 to about 30:1, preferably about 5:1 to about 25:1. In some embodiments, a nanoparticle has a positive to negative charge ratio of about 4:1, about 5:1, about 6:1, about 7:1, or about 8:1. In other embodiments, a nanoparticle has a positive to negative charge ratio of about 10:1, about 11:1, about 12:1, about 13:1, or about 14:1. In yet other embodiments, a nanoparticle has a positive to negative charge ratio of about 22:1, about 23:1, about 24:1, about 25:1, or about 26:1.

As described in Section I(a), a peptide-polynucleotide complex is capable of efficient release of the polynucleotide into the cytoplasm of a cell. A peptide-polynucleotide complex may also be capable of protecting the polynucleotide from degradation upon administration in a subject. As such, a peptide-polynucleotide nanoparticle of the invention may remain stable in the presence of serum. A nanoparticle may remain stable in the presence of serum for about 10, 20, 30, 40, 50, 60 minutes, about 1, 2, 3, 4, 5, 6, 7, 8, 9, 10, 11, 12, 13, 14, 15, 16, 17, 18, 19 hours, about 1, 2, 3, 4, 5, 6, 7 days or longer. A nanoparticle may remain stable in the presence of about 50, 100, 150, 200, or about 300 µg/ml or more human serum albumin. Stability of a nanoparticle may be determined by measuring the ability of a nanoparticle to maintain the activity of a polynucleotide of the peptide-polynucleotide complex of the nanoparticle, or by measuring changes in the size of a nanoparticle over time. Methods of measuring the size of a nanoparticle may be as described in this Section.

Methods of preparing a peptide-polynucleotide complex of the invention generally comprise contacting a peptide of the invention with a polynucleotide of the invention to form a peptide-polynucleotide complex. Typically, a peptide and a polynucleotide are contacted by incubating under conditions suitable for a peptide-polynucleotide complex to form. Conditions suitable for a peptide-polynucleotide complex to form may be as described in the examples. Typically, such conditions may comprise a temperature of about 30° C. to about 40° C., and incubation times of between about 20 sec to about 60 min or more. Suitable temperatures may also be lower than about 30° C. For example, incubation may occur on ice. One skilled in the art will appreciate that the length and temperature of incubation can and will vary depending on the peptide and the polynucleotide, and may be determined experimentally.

A nanoparticle comprising a peptide-polynucleotide complex of the invention may be further modified to enhance stability of the nanoparticle. For instance, a peptide-polynucleotide complex of the invention may be crosslinked to enhance the stability of nanoparticles. One of ordinary skill in the art would recognize that a suitable cross-linker can and will vary depending on the composition of the nanoparticle and the antibody or antibody fragment. In some aspects, a peptide-polynucleotide complex of the invention may be chemically crosslinked using chemical crosslinkers such as glutaraldehyde, bis-carboxylic acid spacers, bis-carboxylic acid-active esters, using a bis-linker amine/acid by carbodiimide coupling protocol, or using a click chemistry protocol, carbodiimde-coupling chemistry, acylation, active ester coupling, or alkylation.

Alternatively, a peptide-polynucleotide complex of the invention may be coated with a compound capable of enhancing the stability of nanoparticles. Methods of modifying a nanoparticle to enhance stability are known in the art, and may be as described in Nicolás et al., 2013 Acta Biomater. 9:4754-4762, the disclosure of which is incorporated herein by reference in its entirety.

As used herein, the term "coating" may refer to the interaction of a peptide-polynucleotide complex with a compound through non-covalent bonds, or to the covalent bonding of a peptide-polynucleotide complex and a compound. In preferred embodiments, a peptide-polynucleotide complex of the invention and a coating compound associate through non-covalent bonds such as a hydrogen bond, an ionic bond, a bond based on Van der Waals, a hydrophobic bond, or electrostatic interactions. For instance, a peptide-polynucleotide complex of the invention may have an overall net positive charge, and a coating compound may have an overall negative charge which may allow the peptide-polynucleotide complex and compound to associate through electrostatic interactions to form a complex of the invention.

Non-limiting examples of compounds that may be used to coat a nanoparticle to enhance stability of the nanoparticle include albumin, fatty acids such as oleic acid, polyethylene glycol, polysaccharides such as chitosan, heparin or heparans and other glycosaminoglycans, or other published coating materials known to those skilled in the art. In some embodiments, stability of a peptide-polynucleotide complex of the invention may be enhanced by coating nanoparticles with a fatty acid. In other embodiments, stability of a peptide-polynucleotide complex of the invention may be enhanced by coating nanoparticles with a polysaccharide.

In preferred embodiments, stability of a nanoparticle comprising a peptide-polynucleotide complex of the invention may be enhanced by coating nanoparticles with albumin. Albumins are negatively charged globular proteins commonly found in blood serum. While not wishing to be bound by theory, it is believed that coating nanoparticles of the invention with albumin may enhance stability of nanoparticles by preventing flocculation. Preferably, albumins that may be used to coat a nanoparticle comprising a peptide-polynucleotide complex of the invention are serum albumins, and may include bovine serum albumin and human serum albumin. In exemplary embodiments, stability of a nanoparticle comprising a peptide-polynucleotide complex of the invention may be enhanced by coating nanoparticles with human serum albumin.

In essence, a nanoparticle is coated with albumin by incubating the nanoparticle with a solution comprising albumin. Nanoparticles may be incubated in a solution comprising about 0.1, 0.2, 0.3, 0.4, 0.5, 0.6, 0.7, 0.8, 0.9, or about 1 mg/ml or more albumin. In some embodiments, nanoparticles comprising a peptide-polynucleotide complex of the invention may be incubated in a solution comprising about 0.1, 0.15, 0.2, 0.25, or about 0.3 mg/ml albumin. In other embodiments, nanoparticles comprising a peptide-polynucleotide complex of the invention may be incubated in a solution comprising about 0.3, 0.35, 0.4, 0.45, or about 0.5 mg/ml albumin. In yet other embodiments, nanoparticles comprising a peptide-polynucleotide complex of the invention may be incubated in a solution comprising about 0.5, 0.55, 0.6, 0.65, or about 0.7 mg/ml albumin. In other embodiments, nanoparticles comprising a peptide-polynucleotide complex of the invention may be incubated in a solution comprising about 0.7, 0.75, 0.8, 0.85, or about 0.9 mg/ml albumin. In additional embodiments, nanoparticles comprising a peptide-polynucleotide complex of the invention may be incubated in a solution comprising about 0.9, 0.95, 1, or about 1.5 mg/ml albumin. In preferred embodiments, nanoparticles comprising a peptide-polynucleotide complex of the invention may be incubated in a solution comprising about 0.4, 0.45, 0.5, 0.55, or about 0.6 mg/ml albumin.

A peptide-polynucleotide complex may be incubated with albumin for about 5, 10, 15, 20, 25, 30, 35, 40, 45, 50, 55, or about 60 minutes or more to coat the peptide-polynucleotide complex. In some embodiments, a particle comprising a peptide-polynucleotide complex of the invention is incubated with albumin for about 5, 10, 15, or about 20 minutes. In other embodiments, a particle comprising a peptide-polynucleotide complex of the invention is incubated with albumin for about 20, 25, 30, or about 35 minutes. In yet other embodiments, a particle comprising a peptide-polynucleotide complex of the invention is incubated with albumin for about 35, 40, 45, or about 50 minutes. In other embodiments, a particle comprising a peptide-polynucleotide complex of the invention is incubated with albumin for about 50, 55, or about 60 minutes or more. In preferred embodiments, a particle comprising a peptide-polynucleotide complex of the invention is incubated with albumin for about 25, 30, or about 35 minutes.

(d) Cell

In another aspect of the invention, a peptide-polynucleotide complex of the invention is capable transfecting the polynucleotide into the cytoplasm of a cell. In some embodiments, a cell is a prokaryotic cell. In preferred embodiments, a cell is a eukaryotic cell. A cell may be in vitro, in vivo, in situ, or ex vivo. A cell may be a single cell, or may comprise a tissue or an organ. The term "cell" also refers to a cell in a subject.

A peptide-polynucleotide complex of the invention may be administered to a cell in vitro by incubating a cell in the presence of a peptide-polynucleotide complex of the invention under conditions suitable for transfection of a polynucleotide of a peptide-polynucleotide complex. Conditions suitable for transfection of a polynucleotide in a peptide-polynucleotide complex may be as described in the examples. One skilled in the art will appreciate that the length of incubation can and will vary depending on the peptide-polynucleotide complex, and the cells. Typically, such conditions may comprise incubation times of between about ten minutes and 24 hours. More preferably, transfection conditions may comprise incubation times of between about 15 minutes and 3 hours.

A peptide-polynucleotide complex of the invention may be administered to a cell in vivo (i.e. in a subject) by administering to a subject a composition comprising a peptide-polynucleotide complex of the invention. Suitable compositions are described in further detail in Section II below.

II. Pharmaceutical Composition

In another aspect of the invention, a peptide-polynucleotide complex of the invention may be incorporated into pharmaceutical compositions suitable for administration. A pharmaceutical composition of the invention may be used to disrupt the expression of one or more than one nucleic acid sequence normally expressed in a cell. For instance, a pharmaceutical composition of the invention may be used to disrupt the expression of 1, 2, 3, 4, 5, 6, 7, 8, 9, 10 or more nucleic acid sequences normally expressed in a cell. A skilled artisan will appreciate that pharmaceutical compositions may be administered to treat a disease, to prevent a disease, or to promote good health. As such, a pharmaceutical composition of the invention may be used to disrupt expression of any nucleic acid sequence normally expressed in a cell, such that disrupted expression leads to measurable and beneficial effects for the subject administered the composition (i.e. significant efficacy)

In some embodiments, a pharmaceutical composition of the invention is used to disrupt the expression of one nucleic acid sequence normally expressed in a cell. In a preferred embodiment, a pharmaceutical composition of the invention is used to disrupt the expression of a nucleic acid sequence encoding STAT3. In another preferred embodiment, a pharmaceutical composition of the invention is used to disrupt the expression of a nucleic acid sequence encoding JNK2. In yet another preferred embodiment, a pharmaceutical composition of the invention is used to disrupt the expression of a nucleic acid sequence encoding the p65 subunit of the canonical NFκB signaling pathway. In another preferred embodiment, a pharmaceutical composition of the invention is used to disrupt the expression of a nucleic acid sequence encoding the p100/p52 subunit of the canonical NFκB signaling pathway.

In other embodiments, a pharmaceutical composition of the invention is used to disrupt the expression of two nucleic acid sequences normally expressed in a cell. In a preferred embodiment, a pharmaceutical composition of the invention is used to disrupt the expression of a nucleic acid sequence encoding the p65 subunit of the canonical NFκB signaling pathway, and a nucleic acid sequence encoding the p100/p52 subunit of the canonical NFκB signaling pathway.

When a pharmaceutical composition of the invention is used to disrupt the expression of more than one nucleic acid sequence normally expressed in a cell, a pharmaceutical composition may be formulated using a mixture of more than one peptide-polynucleotide complex, wherein each complex comprises a polynucleotide capable of disrupting the expression of a different nucleic acid sequence normally expressed in a cell. Alternatively, more than one polynucleotide may be used for generating a mixture of peptide-polynucleotide complexes, wherein each polynucleotide is capable of disrupting the expression of a different nucleic acid sequence normally expressed in a cell.

A pharmaceutical composition of the invention may also comprise one or more nontoxic pharmaceutically acceptable carriers, adjuvants, excipients, and vehicles as desired. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with nanoparticles of the invention, use thereof in the compositions is contemplated. Supplementary active compounds may also be incorporated into the compositions.

A pharmaceutical composition of the invention may be formulated to be compatible with its intended route of administration. Suitable routes of administration include parenteral, oral, pulmonary, transdermal, transmucosal, and rectal administration. The term parenteral, as used herein, includes subcutaneous, intravenous, intramuscular, intrathecal, or intrasternal injection, or infusion techniques.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH may be adjusted with acids or bases, such as hydrochloric acid or sodium hydroxide. The parenteral preparation may be enclosed in ampoules, disposable syringes or multiple dose vials made of glass or plastic.

Oral compositions generally may include an inert diluent or an edible carrier. Oral compositions may be enclosed in gelatin capsules or compressed into tablets. For the purpose of oral therapeutic administration, the active compound may be incorporated with excipients and used in the form of tablets, troches, or capsules. Oral compositions may also be prepared using a fluid carrier for use as a mouthwash, wherein the compound in the fluid carrier is applied orally and swished and expectorated or swallowed. Pharmaceutically compatible binding agents and/or adjuvant materials may be included as part of the composition. The tablets, pills, capsules, troches, and the like, may contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressured container or dispenser which contains a suitable propellant, e.g., a gas such as carbon dioxide, or a nebulizer.

In preferred embodiments, a pharmaceutical composition of the invention is formulated to be compatible with parenteral administration. For instance, pharmaceutical compositions suitable for injectable use may include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.), or phosphate buffered saline (PBS). In exemplary embodiments, a pharmaceutical composition of the invention is formulated with phosphate buffered saline (PBS).

In all cases, a composition may be sterile and may be fluid to the extent that easy syringeability exists. A composition may be stable under the conditions of manufacture and storage, and may be preserved against the contaminating action of microorganisms such as bacteria and fungi. The carrier may be a solvent or dispersion medium containing, for example, water, ethanol, polyol (for example, glycerol, propylene glycol, and liquid polyetheylene glycol, and the like), and suitable mixtures thereof. The proper fluidity may be maintained, for example, by the use of a coating such as lecithin, by the maintenance of the required particle size in the case of dispersion, and by the use of surfactants. Prevention of the action of microorganisms may be achieved by various antibacterial and antifungal agents, for example, parabens, chlorobutanol, phenol, ascorbic acid, thimerosal, and the like. In many cases, it may be preferable to include isotonic agents, for example, sugars, polyalcohols such as mannitol, sorbitol, or sodium chloride, in the composition. Prolonged absorption of the injectable compositions may be brought about by including in the composition an agent which delays absorption, for example, aluminum monostearate and gelatin.

Sterile injectable solutions may be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Systemic administration may also be by transmucosal or transdermal means. For transmucosal or transdermal administration, penetrants appropriate to the barrier to be permeated are used in the formulation. Such penetrants are generally known in the art, and may include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds may also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylactic acid. Methods for preparation of such formulations will be apparent to those skilled in the art. These may be prepared according to methods known to those skilled in the art, for example, as described in U.S. Pat. No. 4,522,811.

Additional formulations of pharmaceutical compositions may be in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y.

(1980). Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

One of skill in the art will recognize that the concentration of a peptide-polynucleotide complex of the invention in a pharmaceutical composition can and will vary depending in part on the route of administration, the subject, and the reason for the administration, and may be determined experimentally. Methods of experimentally determining the concentration of an active agent such as nanoparticles of the invention in a pharmaceutical composition are known in the art. In general, a pharmaceutical composition may be formulated to comprise about 0.1 nM to about 50 µM of a polynucleotide in a peptide-polynucleotide complex of the invention. For example, a pharmaceutical composition may be formulated to comprise about 0.1 nm, 0.2 nm, 0.3 nm, 0.4 nm, 0.5 nm, 0.6 nm, 0.7 nm, 0.8 nm, 0.9 nm, 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, 101 nm, 102 nm, 103 nm, 104 nm, 105 nm, 106 nm, 107 nm, 108 nm, 109 nm, 110 nm, 111 nm, 112 nm, 113 nm, 114 nm, 115 nm, 116 nm, 117 nm, 118 nm, 119 nm, 120 nm, 121 nm, 122 nm, 123 nm, 124 nm, 125 nm, 126 nm, 127 nm, 128 nm, 129 nm, 130 nm, 131 nm, 132 nm, 133 nm, 134 nm, 135 nm, 136 nm, 137 nm, 138 nm, 139 nm, 140 nm, 141 nm, 142 nm, 143 nm, 144 nm, 145 nm, 146 nm, 147 nm, 148 nm, 149 nm, 150 nm, 151 nm, 152 nm, 153 nm, 154 nm, 155 nm, 156 nm, 157 nm, 158 nm, 159 nm, 160 nm, 161 nm, 162 nm, 163 nm, 164 nm, 165 nm, 166 nm, 167 nm, 168 nm, 169 nm, 170 nm, 171 nm, 172 nm, 173 nm, 174 nm, 175 nm, 176 nm, 177 nm, 178 nm, 179 nm, 180 nm, 181 nm, 182 nm, 183 nm, 184 nm, 185 nm, 186 nm, 187 nm, 188 nm, 189 nm, 190 nm, 191 nm, 192 nm, 193 nm, 194 nm, 195 nm, 196 nm, 197 nm, 198 nm, 199 nm, 200 nm, 201 nm, 202 nm, 203 nm, 204 nm, 205 nm, 206 nm, 207 nm, 208 nm, 209 nm, 210 nm, 211 nm, 212 nm, 213 nm, 214 nm, 215 nm, 216 nm, 217 nm, 218 nm, 219 nm, 220 nm, 221 nm, 222 nm, 223 nm, 224 nm, 225 nm, 226 nm, 227 nm, 228 nm, 229 nm, 230 nm, 231 nm, 232 nm, 233 nm, 234 nm, 235 nm, 236 nm, 237 nm, 238 nm, 239 nm, 241 nm, 242 nm, 243 nm, 244 nm, 245 nm, 246 nm, 247 nm, 248 nm, 249 nm, 251 nm, 252 nm, 253 nm, 254 nm, 255 nm, 256 nm, 257 nm, 258 nm, 259 nm, 261 nm, 262 nm, 263 nm, 264 nm, 265 nm, 266 nm, 267 nm, 268 nm, 269 nm, 271 nm, 272 nm, 273 nm, 274 nm, 275 nm, 276 nm, 277 nm, 278 nm, 279 nm, 281 nm, 282 nm, 283 nm, 284 nm, 285 nm, 286 nm, 287 nm, 288 nm, 289 nm, 291 nm, 292 nm, 293 nm, 294 nm, 295 nm, 296 nm, 297 nm, 298 nm, 299 nm, 300 nm, 301 nm, 302 nm, 303 nm, 304 nm, 305 nm, 306 nm, 307 nm, 308 nm, 309 nm, 310 nm, 311 nm, 312 nm, 313 nm, 314 nm, 315 nm, 316 nm, 317 nm, 318 nm, 319 nm, 320 nm, 321 nm, 322 nm, 323 nm, 324 nm, 325 nm, 326 nm, 327 nm, 328 nm, 329 nm, 330 nm, 331 nm, 332 nm, 333 nm, 334 nm, 335 nm, 336 nm, 337 nm, 338 nm, 339 nm, 340 nm, 341 nm, 342 nm, 343 nm, 344 nm, 345 nm, 346 nm, 347 nm, 348 nm, 349 nm, 350 nm, 351 nm, 352 nm, 353 nm, 354 nm, 355 nm, 356 nm, 357 nm, 358 nm, 359 nm, 360 nm, 361 nm, 362 nm, 363 nm, 364 nm, 365 nm, 366 nm, 367 nm, 368 nm, 369 nm, 370 nm, 371 nm, 372 nm, 373 nm, 374 nm, 375 nm, 376 nm, 377 nm, 378 nm, 379 nm, 380 nm, 381 nm, 382 nm, 383 nm, 384 nm, 385 nm, 386 nm, 387 nm, 388 nm, 389 nm, 390 nm, 391 nm, 392 nm, 393 nm, 394 nm, 395 nm, 396 nm, 397 nm, 398 nm, 399 nm, 400 nm, 401 nm, 402 nm, 403 nm, 404 nm, 405 nm, 406 nm, 407 nm, 408 nm, 409 nm, 410 nm, 411 nm, 412 nm, 413 nm, 414 nm, 415 nm, 416 nm, 417 nm, 418 nm, 419 nm, 420 nm, 421 nm, 422 nm, 423 nm, 424 nm, 425 nm, 426 nm, 427 nm, 428 nm, 429 nm, 430 nm, 431 nm, 432 nm, 433 nm, 434 nm, 435 nm, 436 nm, 437 nm, 438 nm, 439 nm, 440 nm, 441 nm, 442 nm, 443 nm, 444 nm, 445 nm, 446 nm, 447 nm, 448 nm, 449 nm, 450 nm, 451 nm, 452 nm, 453 nm, 454 nm, 455 nm, 456 nm, 457 nm, 458 nm, 459 nm, 460 nm, 461 nm, 462 nm, 463 nm, 464 nm, 465 nm, 466 nm, 467 nm, 468 nm, 469 nm, 470 nm, 471 nm, 472 nm, 473 nm, 474 nm, 475 nm, 476 nm, 477 nm, 478 nm, 479 nm, 480 nm, 481 nm, 482 nm, 483 nm, 484 nm, 485 nm, 486 nm, 487 nm, 488 nm, 489 nm, 490 nm, 491 nm, 492 nm, 493 nm, 494 nm, 495 nm, 496 nm, 497 nm, 498 nm, 499 nm, 500 nm, 501 nm, 502 nm, 503 nm, 504 nm, 505 nm, 506 nm, 507 nm, 508 nm, 509 nm, 510 nm, 511 nm, 512 nm, 513 nm, 514 nm, 515 nm, 516 nm, 517 nm, 518 nm, 519 nm, 520 nm, 521 nm, 522 nm, 523 nm, 524 nm, 525 nm, 526 nm, 527 nm, 528 nm, 529 nm, 530 nm, 531 nm, 532 nm, 533 nm, 534 nm, 535 nm, 536 nm, 537 nm, 538 nm, 539 nm, 540 nm, 541 nm, 542 nm, 543 nm, 544 nm, 545 nm, 546 nm, 547 nm, 548 nm, 549 nm, 550 nm, 551 nm, 552 nm, 553 nm, 554 nm, 555 nm, 556 nm, 557 nm, 558 nm, 559 nm, 560 nm, 561 nm, 562 nm, 563 nm, 564 nm, 565 nm, 566 nm, 567 nm, 568 nm, 569 nm, 570 nm, 571 nm, 572 nm, 573 nm, 574 nm, 575 nm, 576 nm, 577 nm, 578 nm, 579 nm, 580 nm, 581 nm, 582 nm, 583 nm, 584 nm, 585 nm, 586 nm, 587 nm, 588 nm, 589 nm, 590 nm, 591 nm, 592 nm, 593 nm, 594 nm, 595 nm, 596 nm, 597 nm, 598 nm, 599 nm, 600 nm, 601 nm, 602 nm, 603 nm, 604 nm, 605 nm, 606 nm, 607 nm, 608 nm, 609 nm, 610 nm, 611 nm, 612 nm, 613 nm, 614 nm, 615 nm, 616 nm, 617 nm, 618 nm, 619 nm, 620 nm, 621 nm, 622 nm, 623 nm, 624 nm, 625 nm, 626 nm, 627 nm, 628 nm, 629 nm, 630 nm, 631 nm, 632 nm, 633 nm, 634 nm, 635 nm, 636 nm, 637 nm, 638 nm, 639 nm, 640 nm, 641 nm, 642 nm, 643 nm, 644 nm, 645 nm, 646 nm, 647 nm, 648 nm, 649 nm, 650 nm, 651 nm, 652 nm, 653 nm, 654 nm, 655 nm, 656 nm, 657 nm, 658 nm, 659 nm, 660 nm, 661 nm, 662 nm, 663 nm, 664 nm, 665 nm, 666 nm, 667 nm, 668 nm, 669 nm, 670 nm, 671 nm, 672 nm, 673 nm, 674 nm, 675 nm, 676 nm, 677 nm, 678 nm, 679 nm, 680 nm, 681 nm, 682 nm, 683 nm, 684 nm, 685 nm, 686 nm, 687 nm, 688 nm, 689 nm, 690 nm, 691 nm, 692 nm, 693 nm, 694 nm, 695 nm, 696 nm, 697 nm, 698 nm, 699 nm, 700 nm, 701 nm, 702 nm, 703 nm, 704 nm, 705 nm, 706 nm, 707 nm, 708 nm, 709 nm, 710 nm, 711 nm, 712 nm, 713 nm, 714 nm, 715 nm, 716 nm, 717 nm, 718 nm, 719 nm, 720 nm, 721 nm, 722 nm, 723 nm, 724 nm, 725 nm, 726 nm, 727 nm, 728 nm, 729 nm, 730 nm, 731 nm, 732 nm, 733 nm, 734 nm, 735 nm, 736 nm, 737 nm, 738 nm, 739 nm, 740 nm, 741 nm, 742 nm, 743 nm, 744 nm, 745 nm, 746 nm, 747 nm, 748 nm, 749 nm, 750 nm, 751 nm, 752 nm, 753 nm, 754 nm, 755 nm, 756 nm, 757 nm, 758 nm, 759 nm, 760 nm, 761 nm, 762 nm, 763 nm, 764 nm, 765 nm, 766 nm, 767 nm, 768 nm, 769 nm, 770 nm, 771 nm, 772 nm, 773 nm, 774 nm, 775 nm, 776 nm, 777 nm, 778 nm, 779 nm, 780 nm, 781 nm, 782 nm, 783 nm, 784 nm, 785 nm, 786 nm, 787 nm, 788 nm, 789 nm, 790 nm, 791 nm, 792 nm, 793 nm, 794 nm, 795 nm, 796 nm, 797 nm, 798 nm, 799 nm, 800 nm, 801 nm, 802 nm, 803 nm, 804 nm, 805 nm, 806 nm, 807 nm, 808 nm, 809 nm, 810 nm, 811 nm, 812 nm, 813 nm, 814 nm, 815 nm, 816 nm, 817 nm, 818 nm, 819 nm, 820 nm, 821 nm, 822 nm, 823 nm, 824 nm, 825 nm, 826 nm, 827 nm, 828 nm, 829 nm, 830 nm, 831 nm, 832 nm, 833 nm, 834 nm, 835 nm, 836 nm, 837 nm, 838 nm, 839 nm, 840 nm, 841 nm, 842 nm, 843 nm, 844 nm, 845 nm, 846 nm, 847 nm, 848 nm, 849 nm, 850 nm, 851 nm, 852 nm, 853 nm, 854 nm, 855 nm, 856 nm, 857 nm, 858 nm, 859 nm, 860 nm, 861 nm, 862 nm, 863 nm, 864 nm, 865 nm, 866 nm, 867 nm, 868 nm, 869 nm, 870 nm, 871 nm, 872 nm, 873 nm, 874 nm, 875 nm, 876 nm, 877 nm, 878 nm, 879 nm, 880 nm, 881 nm, 882 nm, 883 nm, 884 nm, 885 nm, 886 nm, 887 nm, 888 nm, 889 nm, 890 nm, 891 nm, 892 nm, 893 nm, 894 nm, 895 nm, 896 nm, 897 nm, 898 nm, 899 nm, 900 nm, 901 nm, 902 nm, 903 nm, 904 nm, 905 nm, 906 nm, 907 nm, 908 nm, 909 nm, 910 nm, 911 nm, 912 nm, 913 nm, 914 nm, 915 nm, 916 nm, 917 nm, 918 nm, 919 nm, 920 nm, 921 nm, 922 nm, 923 nm, 924 nm, 925 nm, 926 nm, 927 nm, 928 nm, 929 nm, 930 nm, 931 nm, 932 nm, 933 nm, 934 nm, 935 nm, 936 nm, 937 nm, 938 nm, 939 nm, 940 nm, 941 nm, 942 nm, 943 nm, 944 nm, 945 nm, 946 nm, 947 nm, 948 nm, 949 nm, 950 nm, 951 nm, 952 nm, 953 nm, 954 nm, 955 nm, 956 nm, 957 nm, 958 nm, 959 nm, 960 nm, 961 nm, 962 nm, 963 nm, 964 nm, 965 nm, 966 nm, 967 nm, 968 nm, 969 nm, 970 nm, 971 nm, 972 nm, 973 nm, 974 nm, 975 nm, 976 nm, 977 nm, 978 nm, 979 nm, 980 nm, 981 nm, 982 nm, 983 nm, 984 nm, 985 nm, 986 nm, 987 nm, 988 nm, 989 nm, 990 nm, 991 nm, 992 nm, 993 nm, 994 nm, 995 nm, 996 nm, 997 nm, 998 nm, 999 nm, 1 µm, 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, 30 µm, 31 µm, 32 µm, 33 µm, 34 µm, 35 µm, 36 µm, 37 µm, 38 µm, 39 µm, 40 µm, 41 µm, 42 µm, 43 µm, 44 µm, 45 µm, 46 µm, 47 µm, 48 µm, 49 µm, or about 50 µm of a polynucleotide in a peptide-polynucleotide complex of the invention. In some embodiments, a pharmaceutical composition may be formulated to comprise about 0.1 nM to about 1.0 nM of a polynucleotide in a peptide-polynucleotide complex of the invention. In other embodiments, a pharmaceutical composition may be formulated to comprise about 1 nM to about 10 nM of a polynucleotide in a peptide-polynucleotide complex of the invention. In other embodiments, a pharmaceutical composition may be formulated to comprise about 1 nM to about 100 nM of a polynucleotide in a peptide-polynucleotide complex of the invention. In other embodiments, a pharmaceutical composition may be formulated to comprise about 1 nM to about 200 nM of a polynucleotide in a peptide-polynucleotide complex of the invention. In other embodiments, a pharmaceutical composition may be formulated to comprise about 1 nM to about 50 nM of a polynucleotide in a peptide-polynucleotide complex of the invention. In other embodiments, a pharmaceutical composition may be formulated to comprise about 10 nM to about 100 nM of a polynucleotide in a peptide-polynucleotide complex of the invention. In other embodiments, a pharmaceutical composition may be formulated to comprise about 10 nM to about 200 nM of a polynucleotide in a peptide-polynucleotide complex of the invention. In other embodiments, a pharmaceutical composition may be formulated to comprise about 50 nM to about 100 nM of a polynucleotide in a peptide-polynucleotide complex of the invention. In other embodiments, a pharmaceutical composition may be formulated to comprise about 50 nM to about 200 nM of a polynucleotide in a peptide-polynucleotide complex of the invention. In other embodiments, a pharmaceutical composition may be formulated to comprise about 100 nM to about 200 nM of a polynucleotide in a peptide-polynucleotide complex of the invention. In other embodiments, a pharmaceutical composition may be formulated to comprise about 150 nM to about 200 nM of a polynucleotide in a peptide-polynucleotide complex of the invention. In other embodiments, a pharmaceutical composition may be formulated to comprise about 200 nM to about 100 nM of a polynucleotide in a peptide-polynucleotide complex of the invention. In other embodiments, a pharmaceutical composition may be formulated to comprise about 500 nM to about 1000 nM of a polynucleotide in a peptide-polynucleotide complex of the invention. In other embodiments, a pharmaceutical composition may be formulated to comprise about 1 µM to about 50 µM of a polynucleotide in a peptide-polynucleotide complex of the invention. A concentration of peptide in a peptide-polynucleotide complex of the invention may be calculated based on the desired concentration of polynucleotide and the ratio of peptide to polynucleotide in the peptide-polynucleotide complex of the invention.

A pharmaceutical composition may also be formulated to comprise about 30, 40, 50, 60, 70, 80, 90, 100, 150, 200, 250, 300, 350, 400, 450, 500, 550, 600, 650, or about 700 µg/ml or more of a peptide-polynucleotide complex of the invention. In some embodiments, a pharmaceutical composition is formulated to comprise 30, 35, 40, 45, 50, 55, 60, 65, 70, 75, 80, 85, 90, 95, or about 100 µg/ml of a peptide-polynucleotide complex of the invention. In other embodiments, a pharmaceutical composition is formulated to comprise 100, 110, 120, 130, 140, 150, 160, 170, 180, 190, 200, 210, 220, 230, 240, 250, 260, 270, 280, 290, or about 300 µg/ml of a peptide-polynucleotide complex of the invention. In yet other embodiments, a pharmaceutical composition is formulated to comprise 300, 310, 320, 330, 340, 350, 360, 370, 380, 390, 400, 410, 420, 430, 440, 450, 460, 470, 480, 490, or about 500 µg/ml of a peptide-polynucleotide complex of the invention. In yet other embodiments, a pharmaceutical composition is formulated to comprise 500, 510, 520, 530, 540, 550, 560, 570, 580, 590, 600, 610, 620, 630, 640, 650, 660, 670, 680, 690, or about 700 µg/ml or more of a peptide-polynucleotide complex of the invention.

III. Method of Use

In another aspect, the invention encompasses a method for using a peptide-polynucleotide complex of the invention to transfect the polynucleotide into the cytoplasm of a cell. In some embodiments, the cell is in vitro. In other embodiments, the cell is in vivo. Thus, the present invention also provides a method for using a peptide-polynucleotide complex of the invention to transfect the polynucleotide into the cytoplasm of a cell in a subject in need thereof. Generally speaking, a method of the invention comprises contacting a cell with a peptide-polynucleotide complex of the invention under conditions suitable for transfection of a polynucleotide. Suitable cells and conditions are described above in Section I. In embodiments where the cell is in vivo, a method of the invention typically comprises administering a pharmaceutical composition comprising a peptide-polynucleotide complex of the invention to a subject in need thereof. Suitable pharmaceutical compositions are described in Section II.

In another aspect, the invention encompasses a method for treating a condition in a subject. The method comprises administering to a subject in need thereof a therapeutically effective amount of a pharmaceutical composition comprising a peptide-polynucleotide complex. A peptide-polynucleotide complex of the invention is capable of efficiently transfecting, or delivering, the polynucleotide of the peptide-polynucleotide complex into a cell of the subject.

In some embodiments, a polynucleotide of the invention comprises non-coding RNA capable of regulating or inhibiting expression of a nucleic acid sequence expressed in a cell. By efficiently transfecting a polynucleotide capable of regulating or inhibiting expression of a nucleic acid sequence expressed in a cell, a method of the invention may be used to treat any condition that can be treated by regulating or inhibiting the expression of a nucleic acid sequence normally expressed in a cell. In some preferred embodiments, the invention encompasses a method of administering a peptide-polynucleotide complex of the invention to a subject to treat an NFκB-mediated condition in the subject. In other preferred embodiments, the invention encompasses a method of administering to a subject a peptide-polynucleotide complex of the invention to treat a condition associated with STAT3 dysregulation in the subject. In other preferred embodiments, the invention encompasses a method of administering to a subject a peptide-polynucleotide complex of the invention to treat a condition associated with JNK2 dysregulation in the subject. Specific diseases?

In other embodiments, a polynucleotide of the invention comprises DNA encoding a protein that is deficient or absent in the subject. Non-limiting examples of diseases characterized by deficient or absent protein in a subject include lower motor neuron diseases, Pompe disease, lysosomal storage disorders, and glioblastoma multiforme. In a preferred embodiment, a polynucleotide of the invention comprises DNA encoding a protein that is deficient or absent in a subject with a lysosomal storage disease. Enzyme replacement therapy is particularly well suited for lysosomal storage diseases, and a peptide-polynucleotide complex of the invention may be used to transfect an expression cassette or vector encoding a protein that is deficient or absent in a subject with a lysosomal storage disease into the cytoplasm of the subject. Lysosomal storage disorders include, but are not limited to, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease (Type I, Type II, Type III), GM1 gangliosidosis (Infantile, Late infantile/Juvenile, Adult/Chronic), I-Cell disease/Mucolipidosis II, Infantile Free Sialic Acid Storage Disease/ISSD, Juvenile Hexosaminidase A Deficiency, Krabbe disease (Infantile Onset, Late Onset), Metachromatic Leukodystrophy, Mucopolysaccharidoses disorders (Pseudo-Hurler polydystrophy/Mucolipidosis IIIA, MPSI Hurler Syndrome, MPSI Scheie Syndrome, MPS I Hurler-Scheie Syndrome, MPS II Hunter syndrome, Sanfilippo syndrome Type A/MPS III A, Sanfilippo syndrome Type B/MPS III B, Sanfilippo syndrome Type C/MPS III C, Sanfilippo syndrome Type D/MPS III D, Morquio Type A/MPS IVA, Morquio Type B/MPS IVB, MPS IX Hyaluronidase Deficiency, MPS VI Maroteaux-Lamy, MPS VII Sly Syndrome, Mucolipidosis I/Sialidosis, Mucolipidosis IIIC, Mucolipidosis type IV), Multiple sulfatase deficiency, Niemann-Pick Disease (Type A, Type B, Type C), Neuronal Ceroid Lipofuscinoses (CLN6 disease (Atypical Late Infantile, Late Onset variant, Early Juvenile), Batten-Spielmeyer-Vogt/Juvenile NCL/CLN3 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pompe disease/Glycogen storage disease type II, Pycnodysostosis, Sandhoff Disease/Adult Onset/GM2 Gangliosidosis, Sandhoff Disease/GM2 gangliosidosis—Infantile, Sandhoff Disease/GM2 gangliosidosis—Juvenile, Schindler disease, Salla disease/Sialic Acid Storage Disease, Tay-Sachs/GM2 gangliosidosis, Wolman disease. In exemplary embodiments, the subject requires treatment for a disease selected from the group consisting of Gaucher disease, Fabry disease, MPS I, MPS II] MPS VI and Glycogen storage disease type II.

The peptide, the polynucleotide and peptide-polynucleotide complex may be as described in Section I. Pharmaceutical compositions comprising a peptide-polynucleotide complex of the invention may be as described in Section II. Methods of administering a peptide-polynucleotide complex of the invention, and methods of treating a condition are described below.

(a) Administration to a Subject in Need Thereof

In an aspect, the present invention encompasses administering a therapeutically effective amount of a pharmaceutical composition to a subject in need thereof. As used herein, the phrase "a subject in need thereof" refers to a subject in need of preventative or therapeutic treatment. A subject may be a rodent, a human, a livestock animal, a companion animal, or a zoological animal. In one embodiment, a subject may be a rodent, e.g., a mouse, a rat, a guinea pig, etc. In another embodiment, a subject may be a livestock animal. Non-limiting examples of suitable livestock animals may include pigs, cows, horses, goats, sheep, llamas and alpacas. In still another embodiment, a subject may be a companion animal. Non-limiting examples of companion animals may include pets such as dogs, cats, rabbits, and birds. In yet another embodiment, a subject may be a zoological animal. As used herein, a "zoological animal" refers to an animal that may be found in a zoo. Such animals may include non-human primates, large cats, wolves, and bears. In a preferred embodiment, a subject is a mouse. In another preferred embodiment, a subject is a human.

As described in Section II, a pharmaceutical composition of the invention is formulated to be compatible with its intended route of administration. Suitable routes of administration include parenteral, oral, pulmonary, transdermal, transmucosal, and rectal administration. In preferred embodiments, a pharmaceutical composition of the invention is administered by injection.

One of skill in the art will recognize that the amount and concentration of the composition administered to a subject will depend in part on the subject and the reason for the administration. Methods for determining optimal amounts are known in the art. In general, the concentration of a peptide-polynucleotide complex of the invention in a pharmaceutical composition may be as described in Section II.

Compositions of the invention are typically administered to a subject in need thereof in an amount sufficient to provide a benefit to the subject. This amount is defined as a "therapeutically effective amount." A therapeutically effective amount may be determined by the efficacy or potency of the particular composition, the disorder being treated, the duration or frequency of administration, the method of administration, and the size and condition of the subject, including that subject's particular treatment response. A therapeutically effective amount may be determined using methods known in the art, and may be determined experimentally, derived from therapeutically effective amounts determined in model animals such as the mouse, or a combination thereof. Additionally, the route of administration may be considered when determining the therapeutically effective amount. In determining therapeutically effective amounts, one skilled in the art may also consider the existence, nature, and extent of any adverse effects that accompany the administration of a particular compound in a particular subject.

When a pharmaceutical composition of the invention is administered to a subject by injection, a composition may be administered to the subject in a bolus in an amount of about 0.1, 0.2, 0.3, 0.4, 0.5, 1, 1.5, 2, 2.5, 3, 3.5, 4, 4.5, 5, 5.5, 6.5, 7, 7.5, 8, 8.5, 9, 9.5, 10, 10.5, 11, 11.5, 12, 12.5, 13, 13.5, 14, 14.5, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, or about 100 mg/kg or more. In some embodiments, a pharmaceutical composition of the invention is administered to a subject in an amount of about 0.1, 0.2, 0.3, 0.4, 0.5, 1, 1.5, 2, 2.5, 3, 3.5, 4, 4.5, or about 5 mg/kg. In other embodiments, a pharmaceutical composition of the invention is administered to a subject in an amount of about 5, 5.5, 6.5, 7, 7.5, 8, 8.5, 9, 9.5, 10, 10.5, 11, 11.5, 12, 12.5, 13, 13.5, 14, 14.5, or about 15 mg/kg. In yet other embodiments, a pharmaceutical composition of the invention is administered to a subject in an amount of about 15, 16, 17, 18, 19, 20, 21, 22, 23, 24, 25, 26, 27, 28, 29, or about 30 mg/kg. In other embodiments, a pharmaceutical composition of the invention is administered to a subject in an amount of about 30, 31, 32, 33, 34, 35, 36, 37, 38, 39, 40, 41, 42, 43, 44, or about 45 mg/kg. In additional embodiments, a pharmaceutical composition of the invention is administered to a subject in an amount of about 45, 46, 47, 48, 49, 50, 60, 70, 80, 90, or about 100 mg/kg or more. In preferred embodiments, a composition is administered to the subject in a bolus in an amount of about 0.5, 0.6, 0.7, 0.8, 0.9, 1, 1.1, 1.2, 1.3, 1.4, or about 1.5 mg/kg.

A composition may also be administered by injecting more than one bolus into the subject over a period of time. For instance, a composition may be administered by injecting 1, 2, 3, 4, 5, 6, 7, 8, 9, 10 or more boluses into the subject. In some embodiments, a composition is administered by injecting 1, 2, 3, 4, or 5 boluses into the subject. In other embodiments, a composition is administered by injecting 5, 6, 7, 8, 9, 10 or more boluses into the subject. In preferred embodiments, a composition is administered by injecting 2, 3, or 4 boluses into the subject. The boluses may be injected about every 1, 2, 3, 4, 5, 6, 7, 8, 9, 10, 11, or about every 12 hours, or they may be injected about every 1, 2, 3, 4, 5, 6, or about every 7 days. In preferred embodiments, boluses may be injected about every day.

(b) Treating a NFκB-Mediated Condition

As described above, a method of the invention may be used to treat a NFκB-mediated condition in a subject. A method of the invention may be used to treat a NFκB-mediated condition in a subject by disrupting the expression of a nucleic acid sequence normally associated with a NFκB signaling pathway. A method of the invention may be used to treat a NFκB-mediated condition in a subject by disrupting the expression of a nucleic acid sequence normally associated with the canonical NFκB signaling pathway, the non-canonical NFκB signaling pathway, or both the canonical and non-canonical NFκB signaling pathway. As described in the examples, the applicants surprisingly discovered that disrupting the expression of a nucleic acid sequence normally associated with the canonical NFκB signaling pathway and the non-canonical NFκB signaling pathway is synergistic. The term "synergistic" refers to an effect in which two or more agents work in synergy to produce an effect that is more than additive of the effects of each agent independently. One measure of synergism can be shown by the Chou-Talalay Combination Index Method. The Chou-Talalay Index method is based on the median-effect equation, and derived from the mass-action law principle, which is the theory that links single entity and multiple entities, and first order and higher order dynamics, encompassing the Michaelis-Menten, Hill, Henderson-Hasselbalch, and Scatchard equations. The Chou-Talalay Combination Index Method gives a combination index (CI) where an additive effect gives a CI=1, synergism gives a CI<1, and antagonism gives a CI>1. See Ting-Chao Chou, 2008, Preclinical versus clinical drug combination studies, Leukemia & Lymphoma, 49:2059-2080.

In some embodiments, a method of the invention is used to treat a NFκB-mediated condition in a subject by disrupting the expression of a nucleic acid sequence normally associated with the canonical NFκB signaling pathway. In an exemplary alternative of the embodiments, a NFκB-mediated condition in a subject is treated by disrupting the expression of a nucleic acid sequence encoding the transcription factor p65 subunit of the canonical NFκB signaling pathway.

In other embodiments, a method of the invention is used to treat a NFκB-mediated condition in a subject by disrupting the expression of a nucleic acid sequence normally associated with the non-canonical NFκB signaling pathway. In an exemplary alternative of the embodiments, a NFκB-mediated condition in a subject is treated by disrupting the expression of a nucleic acid sequence encoding the p100/p52 subunit of the canonical NFκB signaling pathway.

In preferred embodiments, a method of the invention is used to treat a NFκB-mediated condition in a subject by disrupting the expression of a nucleic acid sequence normally associated with the canonical NFκB signaling pathway, and a nucleic acid sequence normally associated with the non-canonical NFκB signaling pathway. In an exemplary alternative of the embodiments, a NFκB-mediated condition in a subject is treated by disrupting the expression of a nucleic acid sequence encoding the transcription factor p65 subunit of the canonical NFκB signaling pathway and disrupting the expression of a nucleic acid sequence encoding the p100/p52 subunit of the canonical NFκB signaling pathway.

The term "NFκB-mediated condition" may be used to describe any condition that may be caused by dysregulation of signaling in a NFκB signaling pathway. Non-limiting examples of NFκB-mediated conditions may include an inflammation disorder, an autoimmune disease, transplant rejection, osteoporosis, cancer, arthritis, Alzheimer's disease, arthritis, atherosclerosis, a viral infection, or ataxia telangiectasia. In some embodiments, a method of the invention is used to treat an inflammation disorder. In other embodiments, a method of the invention is used to treat an autoimmune disease. In yet other embodiments, a method of the invention is used to treat transplant rejection. In other embodiments, a method of the invention is used to treat osteoporosis. In additional embodiments, a method of the invention is used to treat Alzheimer's disease. In other embodiments, a method of the invention is used to treat atherosclerosis. In yet other embodiments, a method of the invention is used to treat a viral infection. In still other embodiments, a method of the invention is used to treat ataxia telangiectasia.

i. Treating Cancer

In preferred embodiments, a method of the invention is used to treat a neoplasm or cancer. The neoplasm may be malignant or benign, the cancer may be primary or metastatic; the neoplasm or cancer may be early stage or late stage. A cancer or a neoplasm may be treated by delivering a nucleic acid sequence to a cancer tumor in a subject. The cancer or neoplasm may be treated by slowing cancer cell growth or killing cancer cells.

In some embodiments, a polynucleotide of a peptide-polynucleotide complex of the invention may treat a cancer or a neoplasm by delivering a polynucleotide of the nanoparticle to a cancer cell in a subject in vivo. Non-limiting examples of neoplasms or cancers that may be treated with a method of the invention may include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-cell lymphoma (cutaneous), T-cell leukemia and lymphoma, testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In a preferred embodiment, a method of the invention is used to treat T-cell leukemia and lymphoma. In an exemplary embodiment, a method of the invention is used to treat Human T-Lymphotropic Virus-1 (HTLV-1) induced adult T-cell leukemia/lymphoma (ATLL).

In other embodiments, a polynucleotide of a peptide-polynucleotide complex of the invention may be delivered to a cancer cell in vitro. For instance, a polynucleotide of a peptide-polynucleotide complex of the invention may be delivered to a cancer cell line in vitro. A cancer cell may be a cancer cell line cultured in vitro. In some alternatives of the embodiments, a cancer cell line may be a primary cell line that is not yet described. Methods of preparing a primary cancer cell line utilize standard techniques known to individuals skilled in the art. In other alternatives, a cancer cell line may be an established cancer cell line. A cancer cell line may be adherent or non-adherent, or a cell line may be grown under conditions that encourage adherent, non-adherent or organotypic growth using standard techniques known to individuals skilled in the art. A cancer cell line may be contact inhibited or non-contact inhibited.

In some embodiments, the cancer cell line may be an established human cell line derived from a tumor. Non-limiting examples of cancer cell lines derived from a tumor may include the osteosarcoma cell lines 143B, CAL-72, G-292, HOS, KHOS, MG-63, Saos-2, and U-2 OS; the prostate cancer cell lines DU145, PC3 and Lncap; the breast cancer cell lines MCF-7, MDA-MB-438 and T47D; the myeloid leukemia cell line THP-1, the glioblastoma cell line U87; the neuroblastoma cell line SHSY5Y; the bone cancer cell line Saos-2; the colon cancer cell lines WiDr, COLO 320DM, HT29, DLD-1, COLO 205, COLO 201, HCT-15, SW620, LoVo, SW403, SW403, SW1116, SW1463, SW837, SW948, SW1417, GPC-16, HCT-8HCT 116, NCI-H716, NCI-H747, NCI-H508, NCI-H498, COLO 320HSR, SNU-C2A, LS 180, LS 174T, MOLT-4, LS513, L51034, LS411N, Hs 675.T, CO 88BV59-1, Co88BV59H21-2, Co88BV59H21-2V67-66, 1116-NS-19-9, TA 99, AS 33, TS 106, Caco-2, HT-29, SK-CO-1, SNU-C2B and SW480; B16-F10, RAW264.7, the F8 cell line, and the pancreatic carcinoma cell line Panc1. In an exemplary embodiment, a peptide-polynucleotide complex of the invention may be administered to a F8 cell line. In another exemplary embodiment, a peptide-polynucleotide complex of the invention may be administered to a B16-F10 cell line.

ii. Treating an Arthritic Condition

In other preferred embodiments, a method of the invention is used to treat an arthritic condition. Non-limiting examples of arthritic conditions include osteoarthritis, rheumatoid arthritis, gout and pseudo-gout, septic arthritis, ankylosing spondylitis, juvenile idiopathic arthritis, still's disease, lupus, or arthritis caused by an infection or treatment. In some embodiments, a method of the invention is used to treat osteoarthritis. In other embodiments, a method of the invention is used to treat rheumatoid arthritis. In yet other embodiments, a method of the invention is used to treat gout. In other embodiments, a method of the invention is used to treat pseudo-gout. In additional embodiments, a method of the invention is used to treat septic arthritis. In other embodiments, a method of the invention is used to treat ankylosing spondylitis. In still other embodiments, a method of the invention is used to treat juvenile idiopathic arthritis. In other embodiments, a method of the invention is used to treat still's disease. In additional embodiments, a method of the invention is used to treat lupus. In yet other embodiments, a method of the invention is used to treat arthritis caused by an infection or treatment. For instance, a method of the invention may be used to treat arthritis caused by collagen antibody induced arthritis.

As used herein, the term "treating an arthritic condition" may be used to describe relieving arthritic symptoms. Non-limiting examples of arthritic symptoms, regardless of the type of arthritis, include varied levels of pain, swelling, joint stiffness, inability to use the hand or walk, malaise and a feeling of tiredness, weight loss, poor sleep, muscle aches and pains, tenderness, and difficulty moving the joint. Methods of measuring arthritic symptoms are well known in the art, and may include measuring the thickness of an arthritic joint such as the ankle, using an arthritic score, or using image-based measurements.

In some embodiments, arthritic symptoms are measured by the thickness of the ankle. As such, treating an arthritic condition using a method of the invention may prevent an increase in ankle thickness in a subject treated with a pharmaceutical composition of the invention when compared to a subject that was not treated with the pharmaceutical composition.

In other embodiments, arthritic symptoms are measured using an arthritic score. Methods of measuring an arthritic score are known in the art and may include the American college of rheumatology (ACR) score, the rheumatoid arthritis severity scale (RASS), or the ACR/EULAR Rheumatoid Arthritis Classification Criteria. As such, treating an arthritic condition using a method of the invention may prevent an increase in arthritic score in a subject treated with a pharmaceutical composition of the invention when compared to a subject that was not treated with the pharmaceutical composition. For instance, treating an arthritic condition using a method of the invention may prevent an increase in arthritic score above about 1, 2, 3, 4, 5, 6, 7, 8, or 9 using the ACR/EULAR Rheumatoid Arthritis Classification Criteria. In preferred embodiments, treating an arthritic condition using a method of the invention may prevent an increase in arthritic score above about 1, 2, or about 3.

In yet other embodiments, arthritic symptoms are measured using image-based measurements. Methods of measuring arthritic symptoms using image-based measurements are known in the art and may include using ultrasonic molecular imaging as described in Hughes et al., 2011 J Acoust Soc Am. 129:3756; Hughes 2011 IEEE Trans Ultrason Ferroelectr Freq Control. 58:2361-2369; Hughes et al., 2007 Ultrasound Med Biol. 33:1236-1243; Hughes et al., 2007 Journal of the Acoustical Society of America. 121: 3542-3557; Hughes et al., 2013 J Acoust Soc Am. 133:283-300; Hughes et al., 2009 Journal of the Acoustical Society of America. 126:2350-2358, the disclosures of which are incorporated herein in their entirety.

(c) Treating Conditions Associated with STAT3 Dysregulation

In some embodiments, the invention encompasses a method of administering to a subject a peptide-polynucleotide complex of the invention to treat a condition associated with STAT3 dysregulation in the subject. In some preferred embodiments, the invention is used to treat a condition associated with STAT3 dysregulation in a subject by disrupting the expression of a nucleic acid sequence encoding STAT3 in the subject. For instance, a method of the invention may be used to treat cancer by disrupting the expression of a nucleic acid sequence encoding STAT3. A cancer or neoplasm may be as described in Section III(c)i. The cancer or neoplasm may be treated by slowing cancer cell growth, or by preventing angiogenesis. In some embodiments, the cancer or neoplasm is treated by slowing cancer cell growth. In other embodiments, the cancer or neoplasm is treated by preventing angiogenesis. The term "angiogenesis" means the formation of new blood vessels in a tissue, the stimulation of endothelial cells to proliferate, or the promotion of survival of proliferating endothelial cells. In a preferred embodiment, the invention is used to treat cancer in a subject by disrupting the expression of a nucleic acid sequence encoding STAT3 in the subject. In an exemplary embodiment, the invention is used to treat cancer in a subject by disrupting the expression of a nucleic acid sequence encoding STAT3 in the subject by slowing cancer cell growth. In another exemplary embodiment, the invention is used to treat cancer in a subject by disrupting the expression of a nucleic acid sequence encoding STAT3 in the subject by preventing angiogenesis.

Disrupting the expression of a nucleic acid sequence encoding STAT3 may reduce the expression level of STAT3 protein. Disrupting the expression of a nucleic acid sequence encoding STAT3 may also reduce the level of a mRNA encoding STAT3. For instance, disrupting the expression of a nucleic acid sequence encoding STAT3 may reduce the level of a mRNA encoding STAT3 by about 1, 2, 3, 4, 5, 6, 7, 8, 9, or about 10 fold or more. In some embodiments disrupting the expression of a nucleic acid sequence encoding STAT3 reduces the level of a mRNA encoding STAT3 by about 1, 2, 3, 4, or about 5 fold. In other embodiments disrupting the expression of a nucleic acid sequence encoding STAT3 reduces the level of a mRNA encoding STAT3 by about 5, 6, 7, 8, 9, or about 10 fold or more.

In general, titration curves measuring the ability of a pharmaceutical composition of the invention to disrupt the expression of a nucleic acid sequence normally expressed in a cell may be performed to determine the $IC_{50}$. For instance, the $IC_{50}$ of a pharmaceutical composition comprising a peptide-polynucleotide complex capable of disrupting the expression of STAT3 in a cell may be about 10, 15, 20, 25, 30, 35, 40, 45, 50, 55, 60, 65, 70, 75, 80, 85, 90, 9, or about 100 nM or more. In some embodiments, the $IC_{50}$ of a pharmaceutical composition comprising a peptide-polynucleotide complex capable of disrupting the expression of STAT3 in a cell is about 10, 15, 20, 25, or about 30 nM. In other embodiments, the $IC_{50}$ of a pharmaceutical composition comprising a peptide-polynucleotide complex capable of disrupting the expression of STAT3 in a cell is about 30, 35, 40, 45, 50, 55, or about 60 nM. In yet other embodiments, the $IC_{50}$ of a pharmaceutical composition comprising a peptide-polynucleotide complex capable of disrupting the expression of STAT3 in a cell is about 60, 65, 70, 75, 80, 85, 90, 9, or about 100 nM or more. In preferred embodiments, the $IC_{50}$ of a pharmaceutical composition comprising a peptide-polynucleotide complex capable of disrupting the expression of STAT3 in a cell is about 40, 45, 50, 55, or about 70 nM.

Disrupting the expression of a nucleic acid sequence encoding STAT3 may prevent angiogenesis. Methods of measuring angiogenesis are known in the art and may be as described in the examples and may include matrigel tube formation assays and transwell cell migration assays. Disrupting the expression of a nucleic acid sequence encoding STAT3 may reduce matrigel tube formation by about 30, 35, 40, 45, 50, 55, 60, 65, 70, 75, 80, 85, 90, or about 95% or more. In some embodiments, disrupting the expression of a nucleic acid sequence encoding STAT3 reduces matrigel tube formation by about 30, 35, 40, 45, or about 50%. In other embodiments, disrupting the expression of a nucleic acid sequence encoding STAT3 reduces matrigel tube formation by about 50, 55, 60, 65, 70, 75, 80, 85, 90, or about 95% or more. In preferred embodiments, disrupting the expression of a nucleic acid sequence encoding STAT3 reduces matrigel tube formation by about 50, 55, 60, 65, or about 70%.

(d) Treating Conditions Associated with JNK2 Dysregulation

In other embodiments, the invention encompasses a method of administering to a subject a peptide-polynucleotide complex of the invention to treat a condition associated with JNK2 dysregulation in the subject. In an exemplary embodiment, the invention is used to treat a condition associated with JNK2 dysregulation in a subject by disrupting the expression of a nucleic acid sequence encoding JNK2 in the subject. For instance, a method of the invention may be used to treat atherosclerosis by disrupting the expression of a nucleic acid sequence encoding JNK2. In some preferred embodiments, atherosclerosis is treated by blocking foam cell formation. Foam cell formation is the hallmark of atherosclerotic plaques, and can become a problem when they accumulate at particular foci thus creating a necrotic center of atherosclerosis. In an exemplary embodiment, a peptide-polynucleotide complex wherein the polynucleotide of the complex is an anti-JNK2 siRNA is used to block foam cell formation.

IV. Kit

Another aspect of the invention encompasses a kit. The kit comprises a first composition comprising a peptide of the invention, and optionally a second composition comprising a polynucleotide. Alternatively, a polynucleotide of interest may be provided by a user of the kit. By following directions provided by the kit, a user of the kit may mix the composition comprising a peptide of the invention and a composition comprising a polynucleotide to form a peptide-polynucleotide complex. The directions of the kit may include instructions to mix the peptide and polynucleotide at a suitable ratio. Suitable ratios are described above in Section I. The kit may also include suitable buffers, water, cross-linking reagents or albumin.

Definitions

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The terms "homologous," "identical," or percent "identity" in relation to two or more peptides, refers to two or more sequences or subsequences that have a specified percentage of amino acid residues that are the same (i.e., about 60% identity, preferably 70%, 75%, 80%, 85%, 90%, 91%7 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). The definition also includes sequences that have deletions and/or additions, as well as those that have substitutions, as well as naturally occurring, e.g., polymorphic or allelic variants, and man-made variants. As described below, the preferred algorithms can account for gaps and the like.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. The term "purified" in some embodiments denotes that a nucleic acid or protein gives rise to essentially one band in an electrophoretic gel. Preferably, it means that the nucleic acid or protein is at least 85% pure, more preferably at least 95% pure, and most preferably at least 99% pure. "Purify" or "purification" in other embodiments means removing at least one contaminant from the composition to be purified. In this sense, purification does not require that the purified compound be homogenous, e.g., 100% pure.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Screening for siRNA Knockdown

Knockdown of B16 cells stably expressing GFP-PEST allowed quick screening for effective siRNA knockdown of GFP expression because the PEST sequence shortens GFP half-life from 26 to 10 hours. Melittin derivatives were chosen based on modifications designed to decrease cytotoxicity as well as improve interactions with oligonucleotides. These peptides were screened for their ability to deliver GFP siRNA for the knockdown of GFP in B16 GFP cells (Table 1, FIG. 1). While mellitin itself was too toxic in this concentration range, p5RHH was able to transfect when used at a ratio of peptide:polynucleotide that is between 50:1 and 200:1 and exhibited GFP knockdown. Surprisingly, p5RWRH did not work at a ratio of 50:1 but was able to transfect when used at a ratio of peptide:polynucleotide that is less than 50:1.

TABLE 1

Melittin along with four derivatives were tested for GFP knockdown.

| | Particle composition (peptide/siRNA) | Charge ratio (+/−) | Able to transfect? |
|---|---|---|---|
| Melittin (SEQ ID NO: 14) GIGAVLKVLTTGLPALISWIKRKRQQ | 62:1 | 6:1 | No |
| | 124:1 | 12:1 | Toxic |
| | 248:1 | 24:1 | Toxic |
| Peptide 5C (SEQ ID NO: 13) VLTTGLPALISWIKRKRQQC | 62:1 | 6:1 | No |
| | 124:1 | 12:1 | No |
| | 248:1 | 24:1 | No |
| Peptide 5RWR (SEQ ID NO: 12) VLTTGLPALISWIKRKRQQRWRRRR | 28:1 | 6:1 | No |
| | 56:1 | 12:1 | No |
| | 112:1 | 24:1 | No |
| Peptide 5RHH (SEQ ID NO: 11) VLTTGLPALISWIRRRHRRHC | 50:1 | 6:1 | Yes |
| | 100:1 | 12:1 | Yes |
| | 200:1 | 24:1 | Yes |
| Peptide 5RWRH (SEQ ID NO: 1) | 28:1 | 6:1 | Yes |
| | 56:1 | 12:1 | No |
| | 112:1 | 24:1 | No |

Example 2: Preparation of Peptide/siRNA Nanoassemblies and Analysis

The melittin derivatives were formulated by Genscript (Piscataway, N.J.), dissolved at 10 mM in RNAse/DNAse free water (Sigma, St. Louis, Mo.) and stored in 4 µl aliquots at −80° C. before use. Transfection complexes were prepared by diluting the peptide 1:200 in phosphate buffered saline (PBS, Sigma), vortexed for 30 seconds, followed by addition of the appropriate amount of siRNA (stock concentration of 10 µM in 1× siRNA buffer (Thermo)) and incubated for 40 minutes at 37° C. with shaking in an Eppendorf Thermomixer R. Resulting nanoparticles were analyzed for siRNA incorporation by resolution on a 12% polyacrylamide gel followed by ethidium bromide staining. Dynamic light scattering (DLS) and zeta potential measurements were performed on a Zeta Plus particle sizer (Brookhaven Instruments, Newton, Mass.). Serum stability analysis was performed by incubating freshly formed peptide/siRNA nanoparticles in 10 mg/ml Human Serum Albumin (HSA, Sigma) overnight followed by DLS and zeta potential measurements.

Example 3: siRNA Transfection

B16F10 and RAW264.7 (ATCC, Manassas, Va.) cell lines can be maintained under standard cell culture conditions (37° C. and 5% $CO_2$ in a humidified incubator) in DMEM (Gibco, Carlsbad, Calif.) supplemented with 10% fetal bovine serum (Gibco). B16F10 cells stably expressing GFP can be produced as follows. B16F10 can be transfected (Lipofectamine 2000, Invitrogen) with a fusion of EGFP (pEGFP-N1, Clontech) and the PEST sequence from mouse ornithine decarboxylase (S421-V461) in pEF6V5HisTOPO (Invitrogen). Cells are selected for four rounds with cell sorting by flow cytometry without antibiotic selection. Typically, an aliquot of cells can be maintained in continuous culture for a month without a noticeable change in EGFP expression level. Human umbilical vein endothelial cells (HUVECs) can be purchased from Lifeline Technologies (Frederick, Md.) and cultured in VascuLife Basal Medium (Lifeline Technologies) supplemented with 5 ng/mL EGF, 5 ng/ml bFGF, 15 ng/mL IGF-1, 50 µg/mL ascorbic acid, 1 µg/mL hydrocortisone hem isuccinate, 0.75 U/mL Heparin Sulfate, 10 mM L-glutamine, 2% fetal bovine serum in accordance with manufacturer instructions.

For transfection, cells can be plated in 6 well plates 12 hours before transfection and cultured under standard cell culture conditions. Peptide/siRNA nanoparticles are prepared and incubated with cells for 4 hours in a final volume of 1 mL Optimem I (Gibco) or appropriate media supplemented with 10% FBS. Transfections are scaled accordingly for cells plated in 12 well plates based on cell culture surface area. After transfection, cells are washed twice with PBS and incubated with standard cell culture medium for another 24-72 hours before analysis. Lipofectamine 2000 can be used in accordance with the manufacturer's protocol. Briefly, Lipofectamine 2000 is diluted in Optimem I to a final concentration of 8.4 µg/ml and incubated at room temperature for 15 minutes. siRNA is then added to the diluted lipid and incubated for another 40 minutes before dilution to 1 mL total volume with Optimem I for transfection. Suitable eGFP siRNA can be purchased from Sigma. siGENOME mouse MAPK9 siRNA1, siGENOME mouse STAT3 siRNA2, and siGENOME human STAT3 siRNA2 gene specific siRNAs can be purchased from Dharmacon (Lafayette, Colo.). Scrambled siRNA can be purchased from Qiagen (Valencia, Calif.).

Transfections can be evaluated by Western blot, Real time PCR, Confocal Microscopy, Flow Cytometry, or other suitable assay known in the art.

What is claimed is:

1. A pharmaceutical composition comprising a peptide-polynucleotide complex, the peptide-polynucleotide complex comprising a molar ratio of peptide:polynucleotide that is less than 50:1, wherein the peptide is (a) non-lytic and capable of affecting the release of a polynucleotide from an endosome of a cell, and (b) comprises an amino acid sequence with at least 80% identity to the amino acid sequence of SEQ ID NO: 1.

2. The composition of claim 1, wherein the molar ratio of peptide to oligonucleotide is chosen from about 5:1 to about 45:1.

3. The composition of claim 2, wherein the molar ratio of peptide to oligonucleotide is about 5:1 to about 35:1, about 10:1 to about 40:1, or about 15:1 to about 45:1.

4. The composition of claim 2, wherein the molar ratio of peptide to oligonucleotide is about 5:1 to about 25:1, about 10:1 to about 30:1, about 15:1 to about 35:1, or about 20:1 to about 40:1, or about 25:1 to about 45:1.

5. The composition of claim 1, wherein the complex is a nanoparticle with a diameter of about 50 nm to about 200 nm.

6. The composition of claim 1, wherein the peptide comprises an amino acid sequence with at least 90% identity to SEQ ID NO: 1.

7. The composition of claim 1, wherein the peptide comprises at least one cationic region and at least one histidine residue located adjacent to or within at least one cationic region of the peptide wherein a cationic region is two or more contiguous basic amino acids.

8. The composition of claim 1, wherein the polynucleotide is a non-coding RNA capable of regulating or inhibiting the expression of a nucleic acid sequence.

9. The composition of claim 8, wherein the polynucleotide is a small interfering RNA (siRNA) or an microRNA (miRNA).

10. The composition of claim 1, wherein the complex is coated with albumin.

11. The composition of claim 1, wherein the polynucleotide of the complex disrupts expression of at least one nucleic acid sequence encoding a protein selected from the group consisting of STAT3, JNK2, p65, and p100/52.

12. A method of delivering a polynucleotide to the cytoplasm of a cell, the method comprising contacting a cell with a peptide-polynucleotide complex, the peptide-polynucleotide complex comprising a molar ratio of peptide:polynucleotide that is less than 50:1, wherein the peptide is (a) non-lytic and capable of affecting the release of a polynucleotide from an endosome of a cell, and (b) comprises an amino acid sequence with at least 80% identity to the amino acid sequence of SEQ ID NO: 1.

13. The method of claim 12, wherein the molar ratio of peptide to oligonucleotide is about 5:1 to about 35:1, about 10:1 to about 40:1, or about 15:1 to about 45:1.

14. The method of claim 12, wherein the molar ratio of peptide to oligonucleotide is about 5:1 to about 25:1, about 10:1 to about 30:1, about 15:1 to about 35:1, or about 20:1 to about 40:1, or about 25:1 to about 45:1.

15. The method of claim 12, wherein the polynucleotide is delivered to the cytoplasm of a cell in a subject in need thereof and the method comprises administering to the subject a therapeutically effective amount of a pharmaceutical composition comprising the peptide-polynucleotide complex.

16. The method of claim 15, wherein:
 (a) the polynucleotide disrupts STAT3 expression in a cell and the subject needs therapeutic treatment to inhibit angiogenesis;
 (b) the polynucleotide disrupts JNK2 expression in a cell and the subject needs therapeutic treatment to inhibit foam cell formation; or
 (c) the polynucleotide disrupts p65 expression in a cell and the subject needs therapeutic treatment for arthritis.

17. A peptide comprising an amino acid sequence that has at least 80% identity to the amino acid sequence of SEQ ID NO: 1, wherein the peptide is non-lytic and capable of affecting the release of a polynucleotide from an endosome of a cell.

18. The peptide of claim 17, wherein the peptide comprises an amino acid sequence has at least 90% identity to the amino acid sequence of SEQ ID NO: 1.

19. The peptide of claim 17, wherein the peptide comprises an amino acid sequence has at least 95% identity to the amino acid sequence of SEQ ID NO: 1.

20. The peptide of claim 17, wherein the peptide comprises the amino acid sequence of SEQ ID NO: 1.

* * * * *

UNITED STATES PATENT AND TRADEMARK OFFICE
CERTIFICATE OF CORRECTION

Page 1 of 1

PATENT NO. : 10,758,627 B2
APPLICATION NO. : 15/738478
DATED : September 1, 2020
INVENTOR(S) : Wickline et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 424 days.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*